(12) United States Patent
Deutschle et al.

(10) Patent No.: US 10,017,294 B2
(45) Date of Patent: Jul. 10, 2018

(54) TRANSPORT AND PACKAGING CONTAINER FOR ACCOMMODATING A PLURALITY OF CONTAINERS FOR MEDICAL, PHARMACEUTICAL OR COSMETIC APPLICATIONS AS WELL AS METHODS AND USES THEREOF

(71) Applicant: SCHOTT AG, Mainz (DE)

(72) Inventors: Gregor Fritz Deutschle, Wiesbaden (DE); Edgar Pawlowski, Stadecken-Elsheim (DE); Joern Wassenberg, Mainz (DE); Kai Wissner, Hirschberg (DE)

(73) Assignee: SCHOTT AG, Mainz (DE)

( * ) Notice: Subject to any disclaimer, the term of this patent is extended or adjusted under 35 U.S.C. 154(b) by 67 days.

(21) Appl. No.: 15/193,774

(22) Filed: Jun. 27, 2016

(65) Prior Publication Data

US 2016/0304238 A1    Oct. 20, 2016

Related U.S. Application Data

(62) Division of application No. 14/573,381, filed on Dec. 17, 2014, now Pat. No. 9,403,619.

(51) Int. Cl.

| *A61L 2/08* | (2006.01) |
| *A61L 2/00* | (2006.01) |

(Continued)

(52) U.S. Cl.
CPC ............... *B65D 11/20* (2013.01); *A61J 1/16* (2013.01); *A61L 2/04* (2013.01); *A61L 2/26* (2013.01); *B32B 3/00* (2013.01); *B32B 3/12* (2013.01); *B65B 5/06* (2013.01); *B65B 7/28* (2013.01); *B65B 7/2842* (2013.01); *B65B 55/06* (2013.01);

(Continued)

(58) Field of Classification Search
CPC ..... A61L 2/16; A61L 2/10; F16N 7/00; B65D 25/02; B01L 3/00
USPC .... 422/26, 28, 300; 206/216, 305, 349, 557, 206/207, 370; 220/529, 628
See application file for complete search history.

(56) References Cited

U.S. PATENT DOCUMENTS

| 832,086 A | 10/1906 | Schweitzer |
| 2,598,492 A | 5/1952 | Boes |

(Continued)

FOREIGN PATENT DOCUMENTS

| DE | 7307208 | 5/1973 |
| DE | 9109016 | 10/1991 |

(Continued)

*Primary Examiner* — Monzer R Chorbaji
(74) *Attorney, Agent, or Firm* — Ohlandt, Greeley, Ruggiero & Perle, L.L.P.

(57) ABSTRACT

Disclosed is a transport and packaging container for accommodating a plurality of cylindrical containers for substances, comprising at least two segments of which each can be handled separately and which can be assembled or stuck together to jointly form the transport and packaging container, wherein a first segment of the at least two segments has a bottom for supporting the plurality of containers, and positioning devices are provided for positioning the plurality of containers in the interior of the transport and packaging container in a regular arrangement in such a manner that a collision of the directly adjacent containers is prevented, and wherein at least one of the segments comprises sealing means.

28 Claims, 23 Drawing Sheets

(51) Int. Cl.
  *B65D 77/00* (2006.01)
  *B65D 85/38* (2006.01)
  *B65D 1/24* (2006.01)
  *A45C 11/26* (2006.01)
  *B65D 6/00* (2006.01)
  *B65B 55/06* (2006.01)
  *B65B 7/28* (2006.01)
  *B65B 5/06* (2006.01)
  *A61J 1/16* (2006.01)
  *A61L 2/26* (2006.01)
  *B32B 3/00* (2006.01)
  *B32B 3/12* (2006.01)
  *A61L 2/04* (2006.01)
  *B65D 25/10* (2006.01)
  *A61M 5/00* (2006.01)

(52) U.S. Cl.
  CPC ...... B65D 25/108 (2013.01); *A61L 2202/182* (2013.01); *A61M 5/008* (2013.01); *B32B 2439/00* (2013.01); *B32B 2439/80* (2013.01)

(56) References Cited

U.S. PATENT DOCUMENTS

| | | |
|---|---|---|
| 5,950,832 A | 9/1999 | Perlman |
| 7,845,496 B2 | 12/2010 | Hession |
| 8,100,263 B2 | 1/2012 | Vanderbush et al. |
| 8,118,167 B2 | 2/2012 | Togashi et al. |
| 8,469,185 B2 | 6/2013 | Nicoletti |
| 2005/0019237 A1* | 1/2005 | Riley .................. A61C 3/04 422/297 |
| 2007/0272587 A1 | 11/2007 | Nguyen et al. |
| 2011/0024419 A1 | 2/2011 | Gabel et al. |
| 2011/0132797 A1 | 6/2011 | Adair et al. |
| 2012/0051986 A1 | 3/2012 | Pavlova et al. |
| 2014/0027333 A1 | 1/2014 | Pawlowski et al. |
| 2014/0027342 A1 | 1/2014 | Pawlowski et al. |

FOREIGN PATENT DOCUMENTS

| | | |
|---|---|---|
| DE | 102012103896 | 11/2013 |
| DE | 102012103899 A1 | 11/2013 |
| EP | 2090324 A1 | 8/2009 |
| EP | 2659922 A2 | 11/2013 |
| FR | 2595667 | 9/1987 |
| GB | 2478703 | 9/2011 |

* cited by examiner

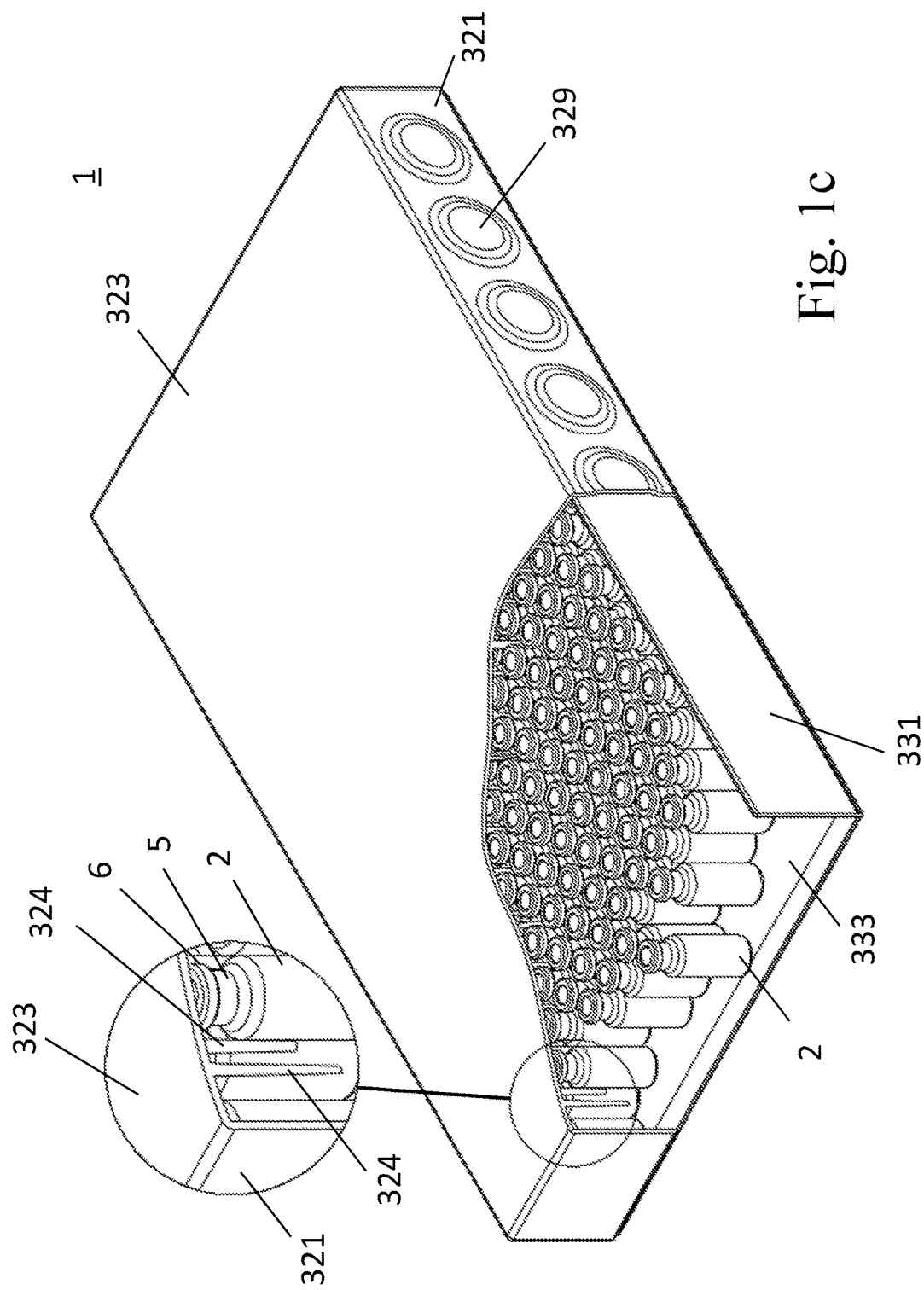

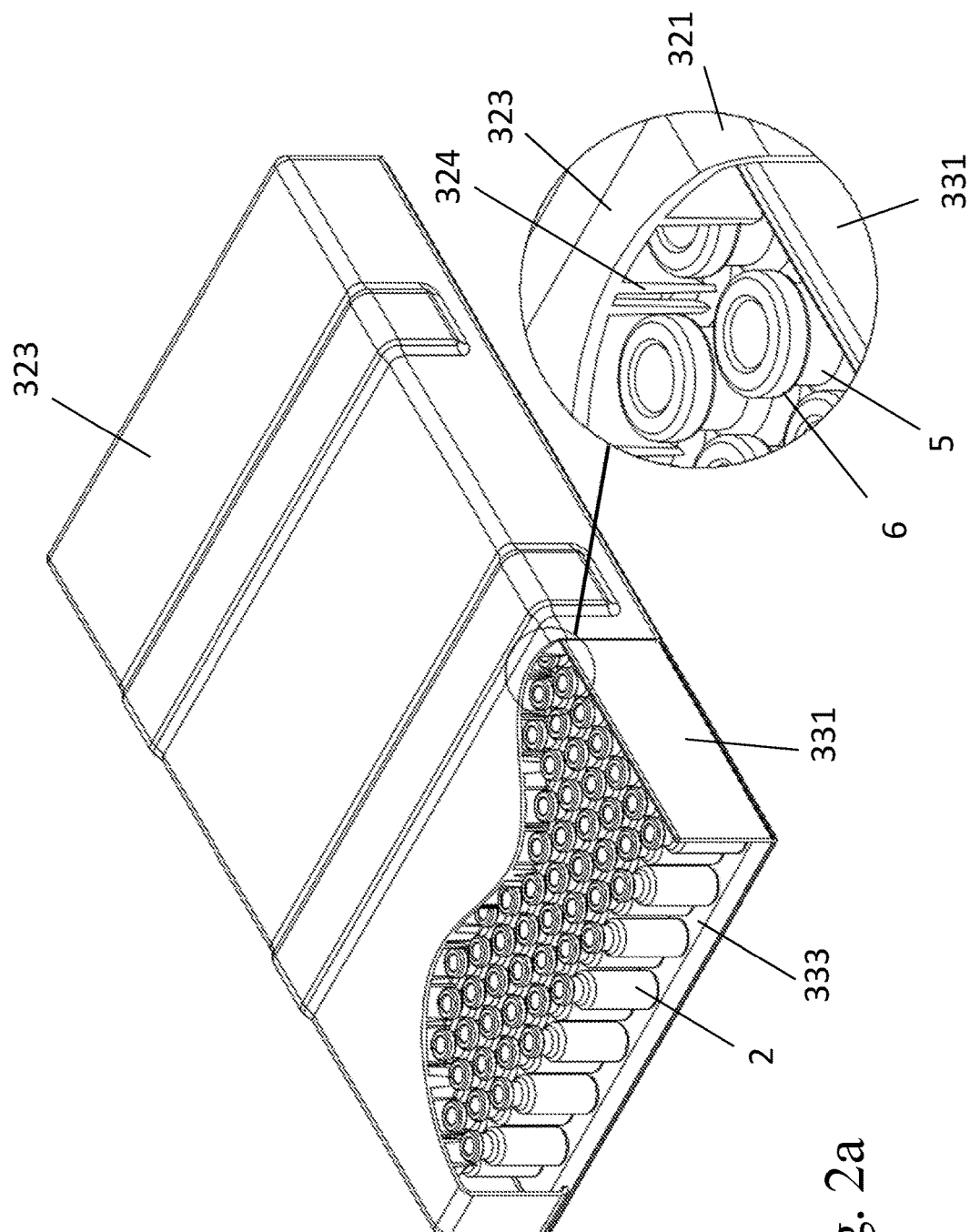

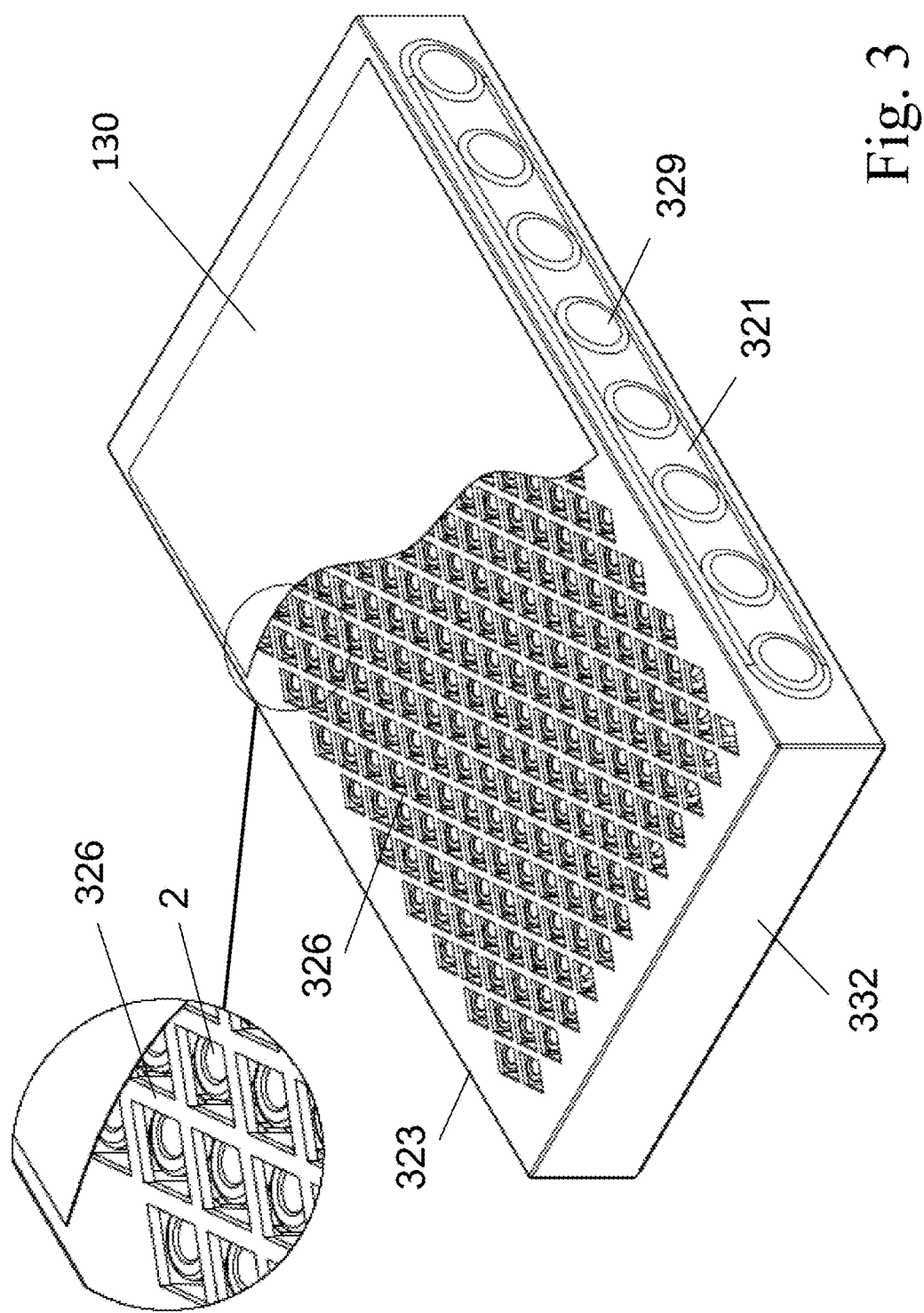

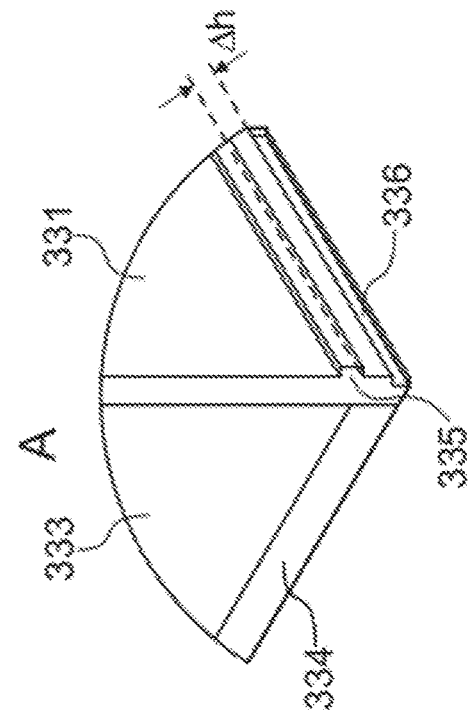
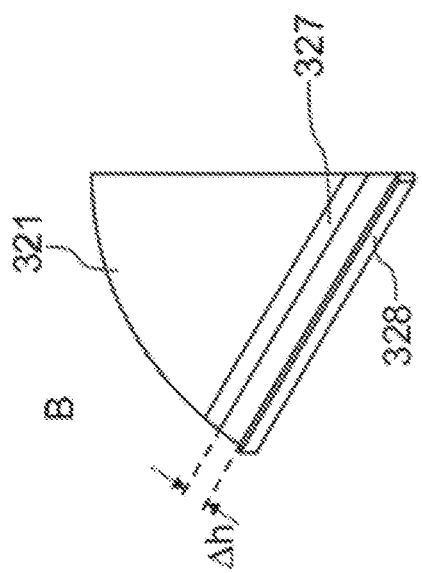
Fig. 4d
Fig. 4c

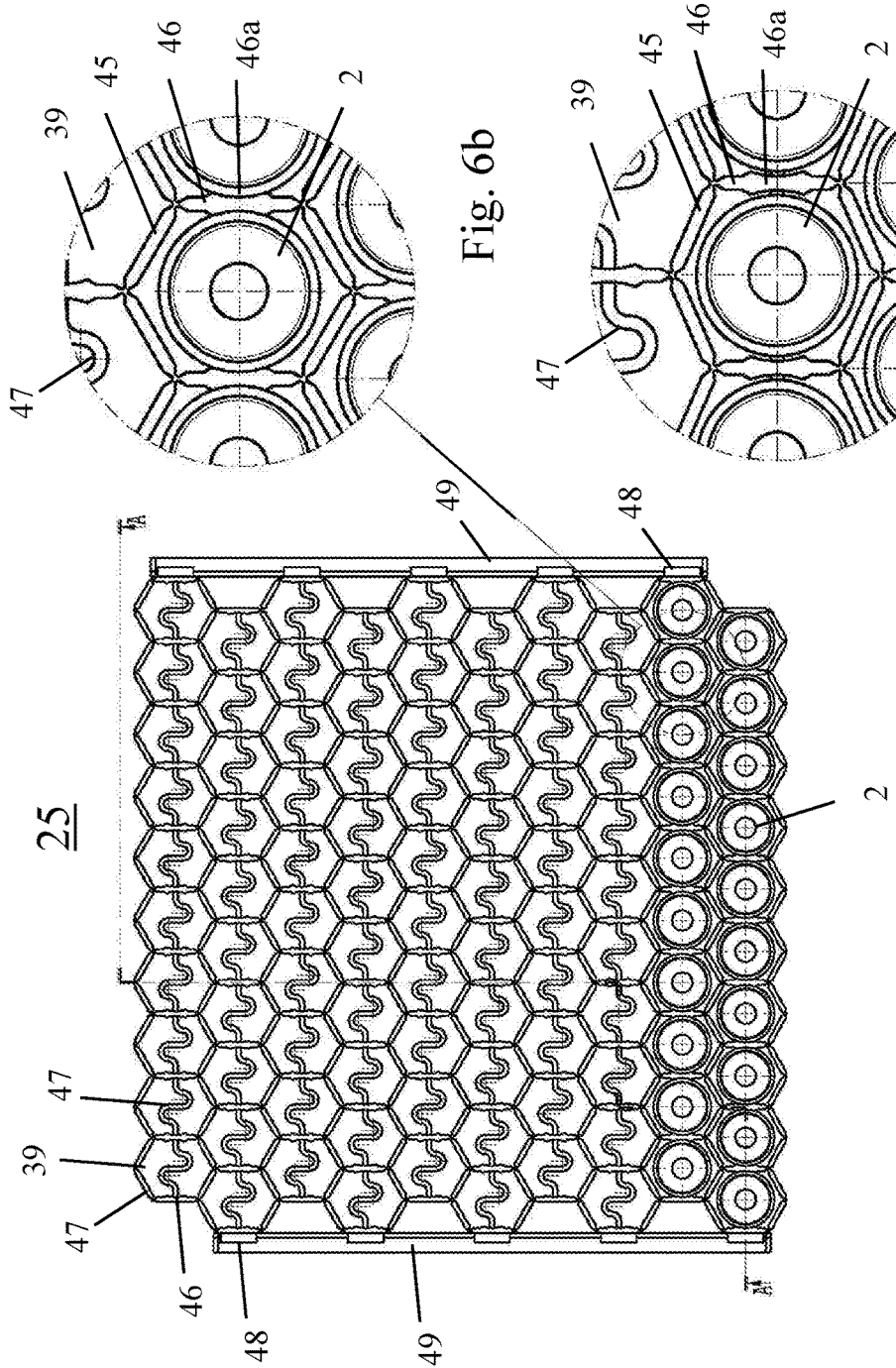

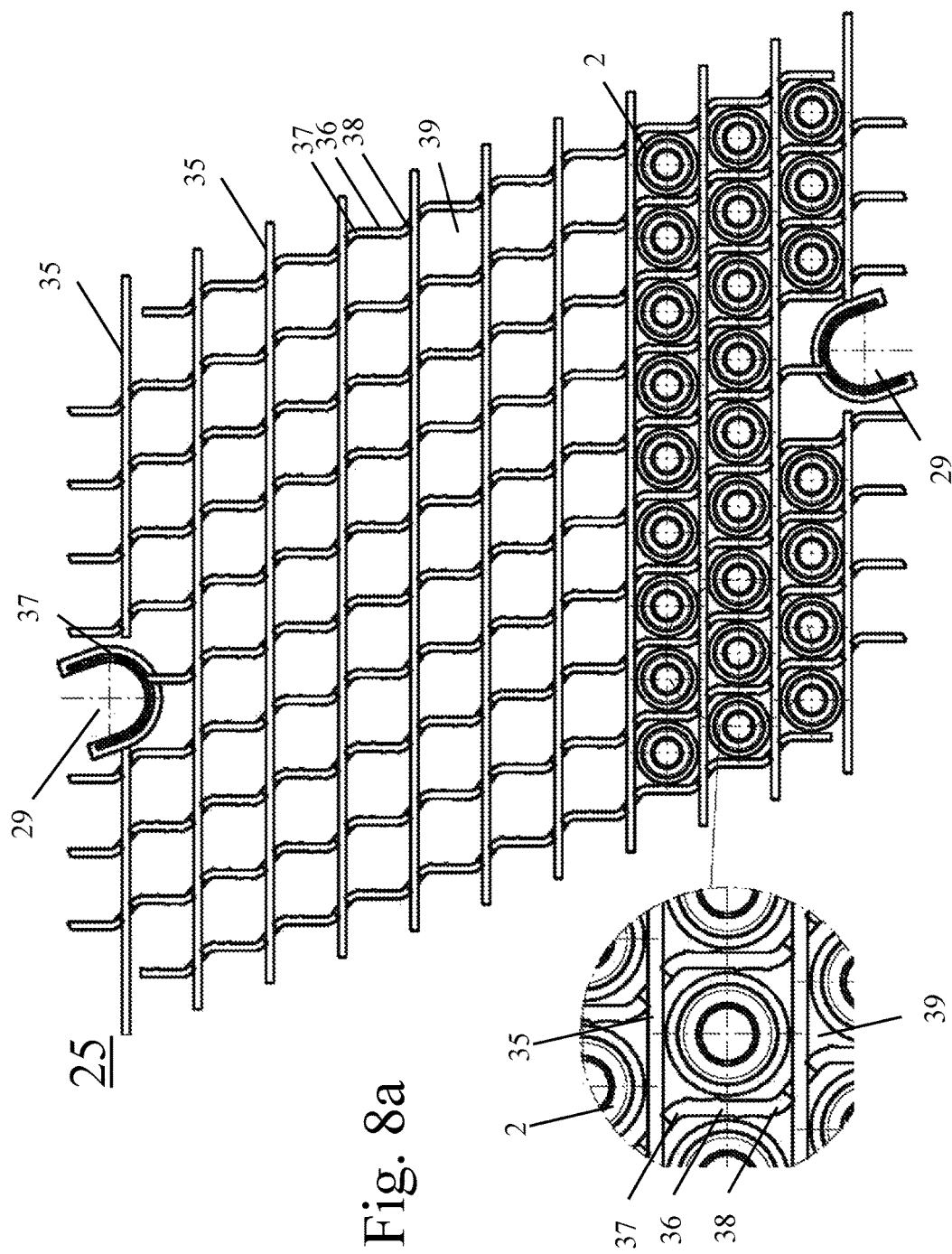

TRANSPORT AND PACKAGING CONTAINER FOR ACCOMMODATING A PLURALITY OF CONTAINERS FOR MEDICAL, PHARMACEUTICAL OR COSMETIC APPLICATIONS AS WELL AS METHODS AND USES THEREOF

CROSS-REFERENCED APPLICATION

This application is a Divisional application of U.S. patent application Ser. No. 14/573,381, filed on 17 Dec. 2014, which is incorporated herein in its entirety by reference. This application claims priority of German patent application no. 10 2013 114 404.7, "Transport and packaging container for accommodating a plurality of containers for medical, pharmaceutical or cosmetic applications as well as methods and uses thereof", filed on 18 Dec. 2013, the whole content of which is hereby incorporated.

BACKGROUND

Field of the Disclosure

The present disclosure relates generally to the concurrent supporting of a plurality of containers for the storage of substances for medical, pharmaceutical or cosmetic applications, in particular of flasks (vials) and cartridges, and more particularly to the concurrent supporting of a plurality of containers in a transport and packaging container in such a manner that these can be further processed in filling units or processing units, in particular in a sterile tunnel, in a filling unit for liquid medical or pharmaceutical applications or in a freeze-dryer.

Background of the Related Art

Medication containers, for example vials, ampoules, syringes or cartridges, are widely used as containers for preservation and storage of medical, pharmaceutical or cosmetic preparations to be administered in liquid form, in particular in pre-dosed amounts. These generally have a cylindrical shape, can be made of plastic material or glass and are available in large quantities at low costs. In order to fill the containers under sterile conditions as efficiently as possible concepts are increasingly used according to which the containers are packaged under sterile conditions in a transport and packaging container already at the manufacturer of the containers, which are then unpacked and further processed under sterile conditions at a pharmaceutical company, in particular in a so-called sterile tunnel.

For this purpose, various transport and packaging containers are known from the prior art, in which a plurality of medication containers are concurrently arranged in a regular arrangement, for example in a matrix arrangement along rows and columns extending perpendicular thereto. This has advantages in the automated further processing of the containers since the containers can be passed to processing stations, for example to processing machines, robots or the like, at controlled positions and in a predetermined arrangement.

Such a transport and packaging container and a corresponding packaging concept are disclosed for example in U.S. Pat. No. 8,118,167 B2. The further processing of the containers is, however, always performed such that the supporting structure will be removed from the transport and packaging container, that the containers will be removed from the supporting structure and isolated and then individually placed on a conveyor, in particular a conveyor belt, and passed to the processing stations for further processing. This limits the speed of processing that can be achieved.

Particularly in the isolation of the containers by means of cell wheels or the like, it always occurs that individual containers abut uncontrolled, which results in an undesired abrasion and subsequently in a contamination of the interior volume of the containers or of the processing station and in an impairment of the outer appearance of the containers, which is undesirable.

GB 2478703 A discloses a supporting structure for supporting a plurality of vials for applications in gas or liquid chromatography. The supporting structure consists of two plates in which a plurality of receptacles is formed for accommodating the vials therein, wherein the two plates can be folded to each other. The receptacles of the two plates are offset from one another, so that the containers are arranged in an interleaved manner to double the packing density and to enable a good access to the containers in the folded-in position. Measures for sealing the interior of a transport container formed by two plates are not disclosed.

Further transport and packing containers and supporting structures are disclosed by U.S. Pat. No. 8,100,263 B2, US 2011/0132797 A1, FR 2595667 and U.S. Pat. No. 832,086 A.

A direct contact with the bottoms of the medication containers is not possible with the conventional supporting structures. However, this impedes the further processing of the medication containers particularly when their content shall be subjected to a freeze-drying process (also known as lyophilization or sublimation drying). Furthermore, a further processing of the medication containers directly within the supporting structures is not possible, because they are supported there either rigidly or are not accessible to a sufficient extent for the further processing, which is the reason why conventionally the medication containers always need to be taken out of the supporting structures for further processing.

A fundamental problem in the production and processing containers for medical or pharmaceutical applications are contaminants, which are resistant to high temperatures, particularly endotoxins, the lysis of bacteria as well as a number of other substances inducing cytokines (CIS). Endotoxins (pyrogens) are lipopolysaccharides from the outer layers of the cell membrane of gram-negative bacteria, for example *E. coli*. In the parenteral administration in human beings endotoxins cause febrile reactions and thus must be avoided by all means. These contaminations naturally occur for example in bacterial fermentation processes, but can be transmitted in part by human beings themselves or by contaminated water systems in the production. Endotoxins are highly temperature resistant and withstand fluctuations in pH. To eliminate such contaminations very high temperatures must be used (especially above 300° C.). In this context, there is still room for improvement with regard to transport and packaging containers or supporting structures thereof, which accommodate or support the containers during their processing at high temperatures, and with regard to procedures for removing such contaminants in containers in a simple and cost-effective manner by processing at high temperatures.

The burning-in of silicones for fixing the silicone on the glass surface has proved to be advantageous to prevent such contaminations in containers for substances for medical or pharmaceutical applications, especially those made of glass. For this purpose, high temperatures of above 300° C. are necessary. For this purpose it is advantageous to carry out the processing of the glass body under clean room conditions. The siliconization provides a protective layer for drugs that are based on sensitive molecules, which can react to the glass container. In this context, there is still room for improvements with regard to transport and packaging containers or supporting structures thereof, which accommodate or support the containers during their processing and during the burning-in of silicone layers at high temperatures, and with regard to procedures for processing the containers and during the burning-in of silicone layers at high temperatures in a simple and cost-effective manner.

SUMMARY

It is an object of the present disclosure to provide an enhanced transport and packaging container which allows a rapid removal or processing of the containers accommodated in the transport and packaging container so that these are ready to be filled, particularly when performing so-called ready-to-fill processes. In particular, the containers shall be sterile packaged, unpackaged and further processed in a simple and cost-effective manner.

It is a further object of the present disclosure to provide a process and use for processing the containers so that they are ready to be filled, particularly in so-called ready-to-fill processes, wherein the containers shall be sterile packaged, unpackaged and further processed in a simple and cost-effective manner.

According to the present disclosure there is provided a transport and packaging container for accommodating a plurality of cylindrical containers for substances for medical, pharmaceutical or cosmetic applications, comprising at least two segments of which each can be handled separately and which can be assembled or stuck together to jointly form the transport and packaging container with an interior, in which the containers can be accommodated sealed against the environment. In this transport and packaging container a first segment of the at least two segments has a bottom for supporting the plurality of containers directly or indirectly on the bottom. Furthermore, positioning devices are provided in the transport and packaging container for positioning the plurality of containers in the interior of the transport and packaging container in a regular arrangement in such a manner that a collision or direct contact of directly adjacent containers is prevented. Here, at least one of the segments comprises sealing means so that the segments can be assembled or stuck together to the transport and packaging container and so that the interior of the transport and packaging container is sealed against the environment.

Thus, the containers are arranged reliably and free of collisions and at predetermined positions in the interior of the transport and packaging container, so that the containers can be transferred easily to automated processing stations and/or can be processed further in such automated processing stations. This further processing may be performed outside of the transport and packaging container, in particular while the plurality of containers is supported in a supporting structure, which is inserted into the transport and packaging container; or the further processing may be performed while the containers are arranged in a segment of the transport and packaging container, for example in a supporting structure, which is placed on the bottom of the segment. Thus, according to the present disclosure it is possible to transport containers of different sizes (length and diameter) and of virtually any shape reliably and without glass-to-glass-contact, particularly vials, syringes, dual-chamber syringes, cartridges, dual-chamber cartridges and vartridges.

Here, the sealing means enables a reliable sealing of the interior of the transport and packaging container against the environment, which may be in principle also configured for a sterile storage of containers in the interior. Preferably, the segments can be drawn out or separated repeatedly and be pushed back or stuck together to the transport and packaging container repeatedly, for example, for the temporary removal of containers for further processing in a processing station and their subsequent packaging, e.g. for a sterile transport to another processing station or to the end customer. Whereas according to the prior art this required the breaking of seals, e.g. of sterile protecting foils, according to the present disclosure the transport and packaging containers can be opened and sealed again virtually for any number of times.

The segments can have almost any shape as long as they can form a closed transport and packaging container in the assembled state. Segments having plate-shaped side walls and/or bottoms have turned out to be of particular use, wherein the side walls preferably form the sidewalls of the transport and packaging container in the assembled state of the segments.

According to a preferred further embodiment, the segments are each jointly formed as drawers that can be pulled out, each consisting of three side walls and a bottom, so that the transport and packaging container can be opened and closed again by pushing the drawers sideward.

In general preference is given to embodiments in which a total of two segments in the manner of drawers form a transport and packaging container that is overall box-shaped. In general it is, however, also possible that in the case of a plurality of segments, which are each designed in the manner of a drawer, respectively one segment is disposed above another segment and these are inserted into each other for jointly forming a transport and packaging container in a stacked arrangement consisting of a plurality of segments, from which the individual drawer-like segments can be removed again.

For this purpose, according to a further embodiment, guide rails and guide recesses are provided preferably at the segments, which are formed corresponding to each other and which guide the segments for assembling the transport and packaging container. Thus, the transport and packaging container can be disassembled and assembled in a particularly simple manner, namely by laterally inserting the segments, which may be performed both manually and automated, e.g. using a robot in a processing station.

Here, according to a further embodiment the guide rails and guide recesses of the segments may also serve for accomplishing the desired sealing of the transport and packaging container. For this purpose, the guide rails or guide recesses may be surrounded by suitable sealing lips that prevent contaminants from entering the interior of the transport and packaging container. Or the guide rails and guide recesses may be provided with a resilient plastic plating, for example, formed by means of a two-component injection molding technology, so that the resilient plastic plating is pressed resiliently against opposite side walls of the guide rails or guide recesses of the other segment in order to seal the interior of the transport and packaging container specifically also in these areas.

For implementing an additional sealing of the interior of the transport and packaging container, according to a further embodiment at least one additional recess or at least one additional protrusion is formed at the bottom edge of the side walls of the respective segment, which serves as an additional sealing means and extends in the longitudinal direction and in parallel with the guide rails and guide recesses, which are provided on the side walls and which are formed corresponding to each other. Thus, particularly the entering of contaminants into the interior of the transport and packaging container near the bottom edge of the transport and packaging container is further prevented. Here, also the additional recess or the additional protrusion may be provided with a resilient plastic plating in the manner described above, which is, for example, formed using a two-component injection molding technology, so that the additional recess or the additional protrusion of the respectively associated guide rail or guide recess is biased resiliently in order to seal the interior of the transport and packaging container specifically in these areas.

For enabling an even quicker and more reliable opening and closing of the transport and packaging container, according to a further embodiment the segments can be locked directly to one another to form the transport and packaging container. In general, this may also be accomplished by means of locking means provided on the outer surface of the transport and packaging container. According to a preferred further embodiment, however, such locking means are provided directly on the segments or such locking means or are formed by them by means of an appropriate design, in particular of the edges or corner regions of the side walls of the segments in order to lock the segments when the segments are assembled or stuck together to form the transport and packaging container. When assembling or sticking together the at least two segments, thus finally the locking means are in mechanical engagement with each other, to cause the aforementioned locking. Conveniently, for this purpose protrusions and corresponding recesses, which cooperate with each other in a positive-fit manner, are formed at the edges or end portions of the side walls of the segments, which can be locked or latched together and which are preferably biased towards each other resiliently, in particular as the result of the material properties of the side walls in this region itself or by means of resilient return members, in particular by means of springs or the like.

According to a further embodiment, resilient sealing means for sealing the interior of the transport and packaging container against the environment are provided on the segments themselves. This can be accomplished by suitable shaping of the edges or corner regions of the side walls of the segments that are opposite to each other and in abutment with each other when the segments are assembled or stuck together to form the transport and packaging container, so that no undesirable air gaps can remain in these areas. It is advantageous if the edges or corner regions of the side walls have a certain elasticity in these areas in order to bias these areas against each other resiliently or to keep them slightly deformed and pressed against each other when the segments are assembled or stuck together to form the transport and packaging container. This can be accomplished by a suitable choice of the material properties of the side walls in these areas or by disposing resilient sealing lips in these areas. Such resilient sealing lips in principle may be inserted as separate sealing members into grooves, which are provided in the afore-mentioned areas, but may also molded to the segments of a softer resilient plastic material in these areas using a two-component (2K) injection molding technology.

According to a further embodiment, the positioning devices (positioning means) are formed directly on at least one of the segments, in particular integrally formed therewith, which can be implemented easily using an injection molding during the production of the segments from plastic material. For this purpose, pins or wall sections that are formed suitably and integral with the respective segment may protrude at a right angle from the inside or form the bottom of the respective segment to prevent a contact of the directly adjacent containers, when these are accommodated in the transport and packaging container.

According to a further embodiment the positioning devices are formed by a carrier or a supporting structure as a separate component that can be inserted into the transport and packaging container and that can be removed again. A plurality of receptacles is formed in the carrier or supporting structure, which are configured such that the containers can be inserted into the associated receptacles from above or from below.

Preferably, the supporting structure or the carrier is configured in such a manner that the containers are supported by friction or clamped. For frictional supporting or clamping the cylindrical containers receptacles are provided, which are preferably formed such that they are circumferential and extend in the longitudinal direction of the containers. As is well-known, a frictional coupling only requires a sufficient normal force onto the surfaces to be coupled together. The mutual displacement between the container and supporting structure is thus prevented as long as the counteracting force caused by the static friction between the supporting structure and the container is not exceeded. The frictional holding effect stops and the surfaces slide on each other, if the tangential load force is greater than the static friction. However, the latter is unlikely for the relatively low weights of the containers to be accommodated in the supporting structure, but may be utilized in order to displace the containers while being supported in the supporting structure from a first position in axial direction to a second position, in which the containers can be processed further, e.g. in which their openings are closed with a stopper or in which an outer cap (for example a beaded cap or crimp) often made from aluminum sheet is placed on the stopper.

Suitably the frictional coupling is accomplished either below the expanded upper rim of the containers, i.e. at its constricted neck or neck portion below the upper rim, or in the region of the cylindrical side wall. Generally, a support of the bottoms of the containers is not necessary, so that an access to the bottom sides (bottoms) of the containers accommodated in the supporting structure is in general possible. In other words, the containers can be processed further batch-wise in the supporting structures, when these are taken out of the transport and packaging container, but remain supported reliably and free of collisions in the supporting structures during the further processing, resulting in significant advantages with regard to processing speed and in benefits for the automation of processing units and thus overall results in even more economical and more cost-efficient processes. The containers can be raised, in particular in axial direction, or rotated in the supporting structure. According to further embodiments the containers can also be lyophilized in the supporting structure, because a direct contact of the bottoms to a cooling finger of a freeze-dryer is possible. Bottoms or upper ends of the containers can be fixed in a simple manner at a height level, so that all bottoms can be arranged in a common plane, which allows a direct contact to planar processing stations, particularly to a cooling finger or a cooling tray of a freeze-dryer.

Here, the supporting structure suitably permits removing the containers towards the upper side or lower side. Since the position of the forced engagement or frictional engagement between the container and the supporting structure can be varied easily, the supporting structure can be used in a very flexible manner also for containers having different outer dimensions, as long as a sufficient normal force for the frictional engagement can be ensured. The containers can in particular be displaced easily in axial direction in the supporting structure, such that containers of different heights can be held in the same supporting structure. The possibility of displacing the containers in the supporting structure in axial direction also enables an easy compensation of tolerances.

According to a further embodiment, the opening widths or the frictional engagement of all receptacles of the supporting structure can be adjusted together by a coordinated adjustment of the side walls of the receptacles. To this end all receptacles of the supporting structure are preferably coupled with each other mechanically so that an adjustment or deformation of the supporting structure results in a coordinated adjustment of the opening widths of all receptacles. To this end the coordinated adjustment is designed such that the side walls of the receptacles can be adjusted by a coordinated adjustment between a first position, in which the containers can be inserted into the receptacles with little effort, and a second position, in which the containers are clamped or fixed by friction in the openings or receptacles of the supporting structure.

According to a further embodiment, at least the bottom of the transport and packaging container is formed of a high-temperature resistant plastic material, in particular of a thermoplastic plastic, which resists temperatures of up to 330° C. and more preferably of up to 350° C., in particular of polyimide (PI), polyetherketone (PEK), polyetheretherketone (PEEK), polyetherketoneketone (PEKK) or polyetherketoneetherketoneketone (PEKEEK). For this purpose the bottom can also be removed temporarily from the other segments of the transport and packaging container. This enables a processing of the containers at very high temperatures.

According to an alternative embodiment, at least the bottom of the transport and packaging container is formed from a metal, wherein the metal is conveniently coated with a plastic material, in particular of a thermoplastic plastic, which resists temperatures of up to 330° C. and more preferably up to 350° C., in particular of polyimide (PI), polyether ketone (PEK), polyetheretherketone (PEEK), polyetherketoneketone (PEKK) or polyetherketoneetherketoneketone (PEKEEK). For this purpose the bottom can also be removed temporarily from the other segments of the transport and packaging container.

According to a further alternative embodiment, at least the bottom of the transport and packaging container is formed of a metal, wherein the metal is applied to the surface together with a base coating material consisting of $SiO_2$, $TiO_2$, $Al_2O_3$ or $ZrO_2$, and then tempered or burnt in. Suitable coating methods are, for example, sputtering, PVD, CVD, sol-gel coating or spray coating.

This enables a processing of the containers at very high temperatures, in particular the thermal destruction of endotoxins, the lysis of the bacteria, as well as a number of other cytokine inducing substances (CIS), as well as burning-in silicones in the containers, in particular in glass containers formed of glass, but also a freeze-drying of substances stored in the containers, while the containers are accommodated in the transport and packaging container, in a segment thereof or in a carrier, which is accommodated or inserted in the transport and packaging container. It is advantageous that it is not necessary to remove the containers from the transport and packaging container or from a carrier accommodated or inserted therein and to isolate them for the processing, but that the containers can be processed directly. A re-insertion of the containers into the positioning devices of the transport and packaging container or of a carrier accommodated therein is thus not necessary according to the disclosure.

According to a further embodiment, side walls of the transport and packaging container are provided at least in sections with openings that are closed by means of a foil, preferably a gas-permeable plastic foil that is bonded or applied in a different manner, in particular a meshwork of synthetic fibers such as polypropylene fibers (PP) or a Tyvek® protective film. The openings may be provided in particular as relatively large openings for example on side walls of the transport and packaging container. Or the side walls are provided in sections with a permeable, grid-like structure to which the plastic foil is then applied as a cover to seal the grid-like structure. Thus, the transport and packaging containers can be sterile sealed by means of the plastic foil. Thus a gas can flow through the openings to sterilize the interior of the transport and packaging container. By means of the foil it is ensured that the interior of the transport and packaging container is sealed sterile against the environment.

According to a further aspect of the present disclosure there is provided a process for the thermal treatment of containers for substances for medical, pharmaceutical or cosmetic applications, using particularly a transport and packaging container as described above and/or a carrier comprising positioning devices as described above, wherein the bottom of the transport and packaging container together with a plurality of cylindrical containers accommodated therein or the carrier together with a plurality of cylindrical containers is processed in a thermal processing station (a station which processes the containers at high temperatures), in particular in a hot oven or in a hot tunnel, at temperatures of up to 330° C. or up to 350° C. It is an advantage that it is not necessary to remove the containers from the transport and packaging container or from a carrier accommodated therein and to isolate the containers for the processing, but that the containers can be processed directly. Thus, a re-insertion of the containers into the positioning devices of the transport and packaging container or of a carrier accommodated therein is not necessary according to the present disclosure.

According to a further embodiment, the method comprises the further steps of: disposing the plurality of containers in the transport and packaging container for positioning the containers by means of the positioning devices in the interior of the transport and packaging container in a regular array so that collisions of directly adjacent containers are prevented; and processing the plurality of containers while they are arranged in the transport and packaging container or in a segment thereof in a thermal processing station, in particular in a hot oven or a hot tunnel, at temperatures of up to 330° C. or up to 350° C. First, the containers that are intended for storing the substances for medical or pharmaceutical applications are inserted in a transport and packaging container, as described above. In this state, the containers may be packaged and transported or stored in a sterile manner, because the transport and packaging container is designed for this purpose. In general, the processing of the containers at very high temperatures can be performed without further opening of the transport and packaging container. According to preferred embodiments, however, the transport and packaging container is disassembled such that the containers arranged in at least one of its segments, if necessary in a carrier disposed in said at least one segment, are accessible for a further processing, for example for the filling of the containers. After the processing at very high temperatures the transport and packaging container is closed by assembling or sticking its segments again together, so that a state can be obtained again in which the containers are packaged sterile and transported or stored in the transport and packaging container.

According to a further embodiment, for this purpose the segments are assembled or stuck together to form again the transport and packaging container so that the sealing means seal the interior of the transport and packaging container against the environment.

According to a further embodiment, the method further comprises the steps of: opening the transport and packaging container by displacing or releasing at least one segment of the plurality of segments of the transport and packaging container so that the interior of the transport and packaging container is accessible for the removal of the carrier together with the plurality of containers supported by it; removing the carrier together with the plurality of containers supported by it out of the transport and packaging container or at least out of a segment thereof; processing of the plurality of containers while they are supported by the carrier in the thermal processing station, in particular in a hot oven or in a hot tunnel, at temperatures of up to 330° C. and preferably of up to 350° C.; placing the carrier together with the plurality of containers supported by it in or on at least one of the segments; and assembling of or sticking together the segments, to jointly form the transport and packaging containers so that the sealing means seal the interior of the transport and packaging container against the environment. Thus, the containers can be processed directly and while they are supported in the receptacles. A re-insertion of the containers into the positioning devices of the carrier is therefore not necessary according to the present disclosure.

According to a further embodiment, the processing of the plurality of containers is performed in a hot oven or hot tunnel at temperatures of up to 330° C. and preferably of up to 350° C. so that endotoxins and/or the lysis of bacteria and/or cytokine inducing substances (CIS) are removed thermally in the containers. A re-insertion of the containers into the positioning devices of the transport and packaging container or of a carrier accommodated therein is therefore not necessary according to the present disclosure.

According to a further embodiment, the processing of the plurality of containers is performed in a hot oven or hot tunnel at temperatures of up to 330° C. and preferably of up to 350° C. so that silicone layers are burned-in on inner surfaces of the containers, in particular of a bottom or a bottom end thereof. A re-insertion of the containers into the positioning devices of the transport and packaging container or of a carrier accommodated therein is therefore not necessary according to the present disclosure.

A further aspect of the present disclosure relates to the use of a transport and packaging container comprising a plurality of containers accommodated therein in a carrier, as described above, for the processing at temperatures of up to 330° C. and preferably of up to 350° C. in a hot oven or hot tunnel.

According to a further embodiment, the processing is performed at temperatures of up to 330° C. and preferably of up to 350° C. in the hot oven or hot tunnel in such a manner that endotoxins and/or the lysis of bacteria and/or cytokine inducing substances (CIS) in the containers can be removed thermally or that silicone layers on the inner surfaces of the containers, in particular on a bottom and a bottom end thereof, can be burned-in. A re-insertion of the containers into the positioning devices of the transport and packaging container or of a carrier accommodated therein is therefore not necessary according to the present disclosure

BRIEF DESCRIPTION OF THE DRAWINGS

The disclosure will now be described by way of example and with reference to the accompanying drawings, from which further features, advantages and problems to be solved will become apparent. In the drawings:

FIGS. 1a-1c show a transport and packaging container according to a first embodiment of the present disclosure;

FIGS. 2a-2b show a transport and packaging container according to a further embodiment of the present disclosure;

FIG. 3 shows a transport and packaging container according to a further embodiment of the present disclosure;

FIGS. 4a-4d show a transport and packaging container according to a further embodiment of the present disclosure, wherein also details of the sealing means are shown.

In the drawings, identical reference numerals designate identical or substantially equivalent elements or groups of elements.

DETAILED DESCRIPTION OF PREFERRED EMBODIMENTS

Figure 1A:
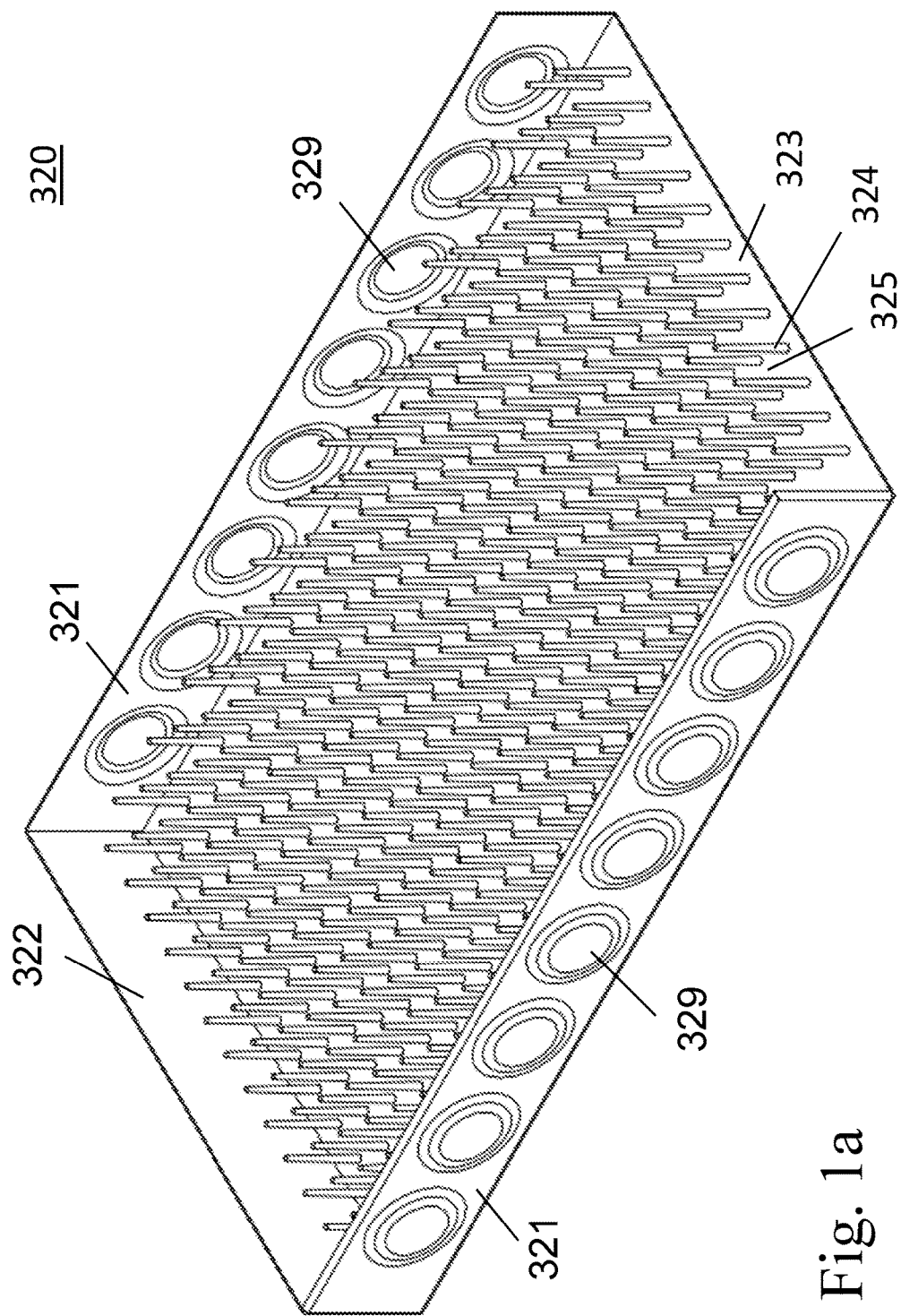

According to the present disclosure, a transport and packaging container with or without an additional supporting structure, as described below, is used for concurrently supporting a plurality of containers for storage of substances for medical, pharmaceutical or cosmetic applications in an array configuration, in particular in a matrix configuration with regular intervals between the containers along two different directions in space, preferably along two mutually orthogonal spatial directions.

An example of such containers embodied as vials is shown schematically in the enlarged inserts in FIGS. 1c and 2a. The vials have a cylindrical basic shape, having a cylindrical side wall 4 with—within tolerances—constant inner and outer diameters, which project vertically from a flat vial bottom 3, which merges in a constricted neck portion 5 of a relatively short axial length near the upper open end of the vial and then merges in a widened upper rim 6, which has a larger outer diameter than the associated neck portion 5 and is configured for connection to a closure member. The neck portion 5 can be formed with smooth walls and without an external thread or may be provided with an external thread for screwing on a closure member. For example, a stopper (not shown) may be inserted in the inner bore of the neck portion 5 and the upper rim 6, whose upper end is connected with the upper rim 6 of the vial in a gas-tight manner and protected against the intrusion of contaminants into the vial, for example by crimping or beading a metal protective foil not shown. Such vials are radially symmetric and are made of a transparent or colored glass or of a suitable plastic material by blow molding or plastic injection molding techniques, and in general can be internally coated so that the material of the vial emits minimal impurities to the agent to be received.

Another example of a medication container in the sense of the present application are ampoules, cartridges and syringes or injection containers.

In the sense of the present disclosure, such containers are used for storage of substances or agents for medical, pharmaceutical or cosmetic applications, which are to be stored in one or several components in solid or liquid form in the container. Especially in the case of glass containers storage periods can amount many years, notably depending on the hydrolytic resistance of the glass type used. While, in the following, cylindrical containers are disclosed, it should be noted that the containers, in the sense of the present disclosure, may also have a different profile, for example a square profile, rectangular profile or polygonal profile.

Inevitably such containers have tolerances due to the production which can be of the order of one or several tenths of a millimeter in particular for glass containers. To compensate for such manufacturing tolerances, while ensuring that all bottoms 3 or bottom ends of the containers can be disposed in a common plane, according to the present disclosure the containers are fixed on a supporting structure 25 by means of a frictional fit or clamping. This frictional fit is implemented either in the region of the cylindrical side wall 4 or at the bottom closed end or bottom of the containers or in accordance with other preferred embodiments in the region of the constricted neck portion 5. In the latter case, at least the great majority of the containers is frictionally supported in the region of the constricted neck portion 5, which, however, according to further embodiments is not intended to exclude that in individual containers with large manufacturing tolerances with respect to their axial length the transition region between the upper rim 6 and the constricted neck portion 5 exceptionally may also be engaged behind or supported in positive fit manner.

For concurrently supporting a plurality of containers, a supporting structure 25 (also referred to as a "nest" in the prior art) is provided, which will be explained hereinafter with reference to FIGS. 1a to 1c and which is formed of a plastic material, e.g. by injection-molding. The supporting structure 25 comprises a plurality of receptacles 39 that extend in the longitudinal direction of the containers 2 to be accommodated and which are coupled with each other. Preferably, the receptacles 39 are also coupled mechanically with each other. The side walls of the receptacles 39 are sufficiently flexible and expandable so that the containers 2 can be inserted from above or from below into the receptacles 39. Thus, a plurality of containers 2 may be supported by friction or may be clamped. Due to the elasticity of the side walls of the receptacles also manufacturing tolerances in the axial and/or radial direction of the containers may be compensated, in particular in the case of medication containers of glass. In particular, containers having different diameters may also be supported by one and the same supporting structure 25 by friction.

Figure 5A:
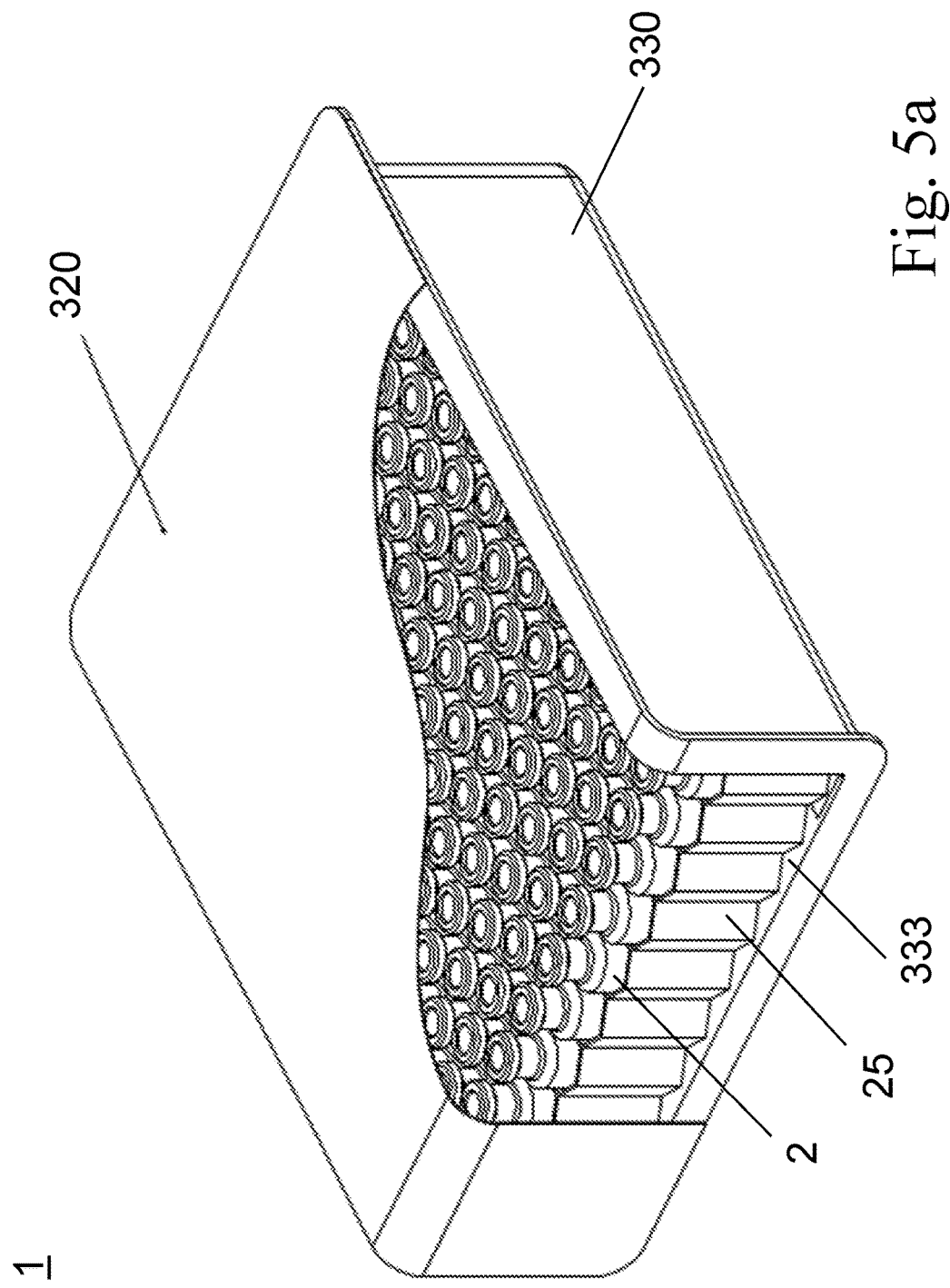
FIGS. 5a-5c show a transport and packaging container according to a further embodiment of the present disclosure.
Figure 5B:
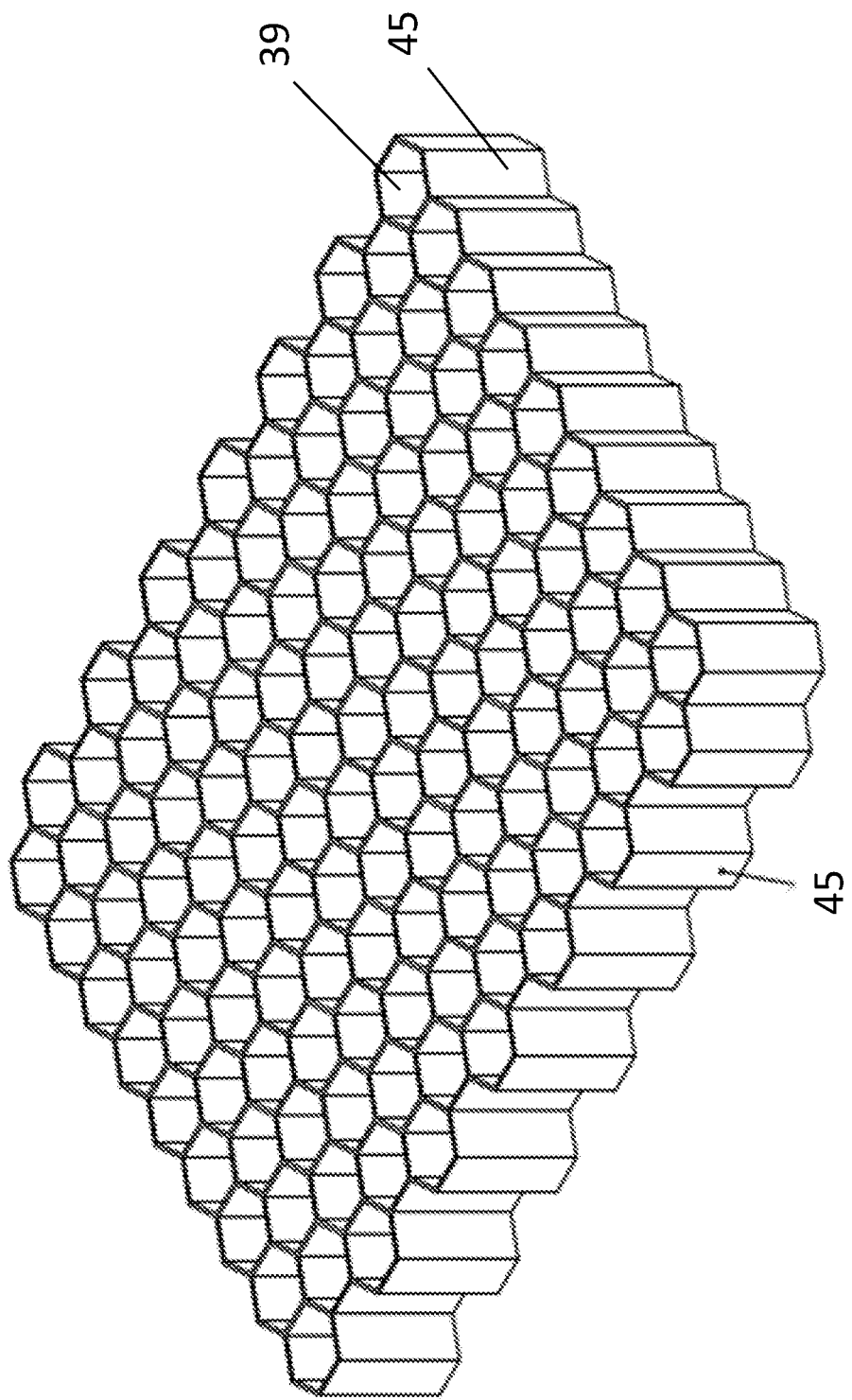

When the containers are inserted into the receptacles 39 of a supporting structure 25 as shown in FIG. 5b, the bottom ends of the containers may protrude by a certain distance beyond the lower rim of the receptacles 39. When the bottom region of the containers is thermally treated by placing it on a heating base, this results in a delayed heating of the material of the supporting structure 25 as a result of the relatively poor thermal conductivity characteristics of the containers (in particular of glass or plastic). This may be sufficient to prevent an overheating of the supporting structure to temperatures above the melting or softening temperature of their material.

For the transport and packaging of a supporting structure in the sense of the present application with the containers accommodated therein a transport and packaging container 1 (referred to as "tub" in the prior art) is used as schematically shown in FIG. 1c. According to FIG. 1c, the container 1 is substantially box-shaped or tub-shaped and comprises a lower segment 330 having a bottom 333 and a side wall and an upper segment 320, wherein the two segments 320, 330 are formed in the manner of drawers having a bottom and three sidewalls protruding perpendicularly therefrom that can be inserted into each other to form the transport and packaging container 1, as described in the following.

Such a transport and packaging container 10 is preferably formed of a plastic material, in particular using plastic injection molding technology, and is preferably formed of a clear transparent plastic material to enable an optical visual inspection of the supporting structure 25 accommodated in the transport and packaging container 10 and of the containers 2 supported by it.

Figure 1B:
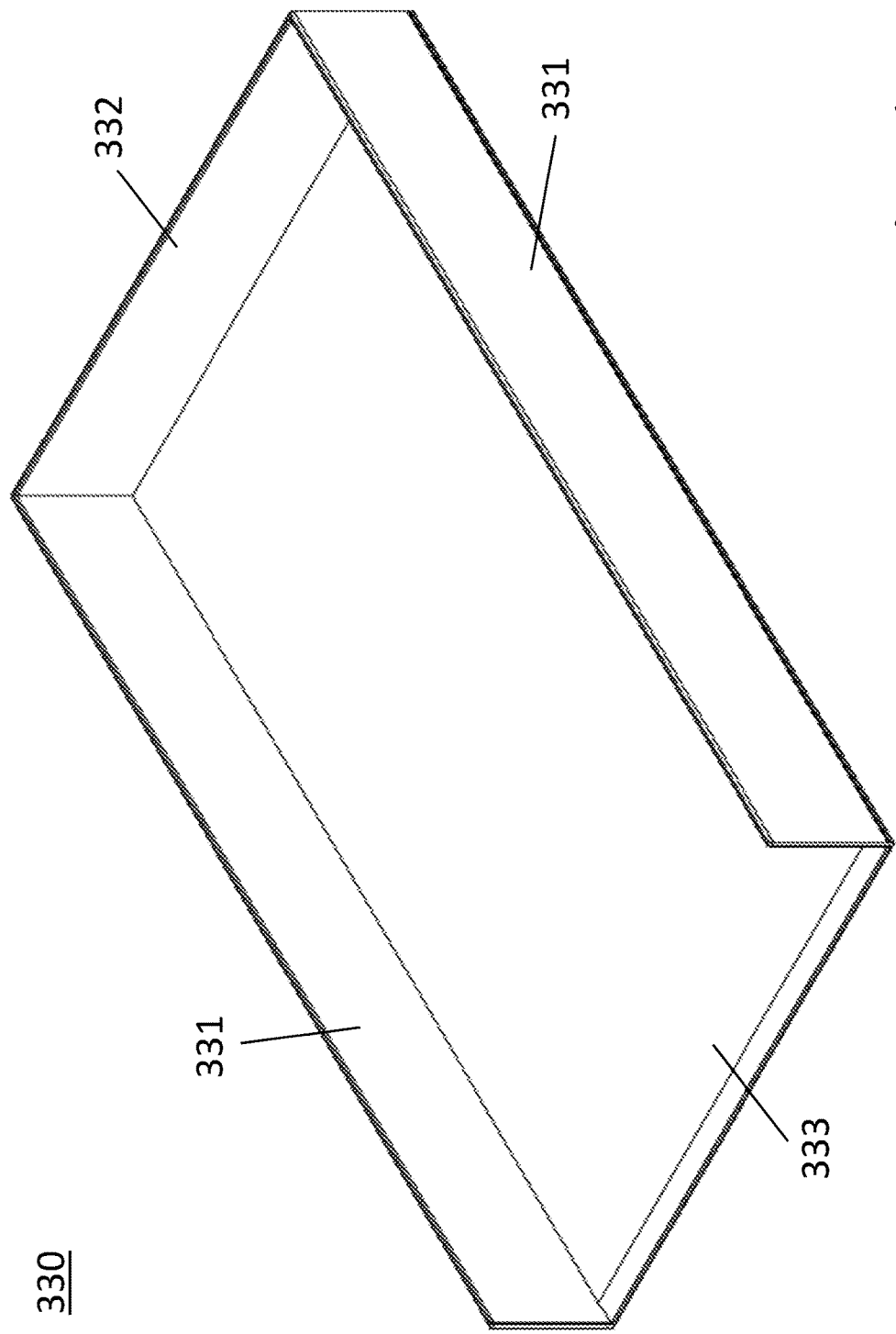

With reference to FIGS. 1a-1c, in the following an embodiment for a transport and packaging container will be described, in which the containers are accommodated without an additional supporting structure, i.e. directly. FIG. 1a shows an upper segment 320 that is formed in the manner of a drawer having a bottom 323, two lateral side walls 321 and a rear side wall 322, both of which protrude at right angles from the bottom 323. Circular openings 329 are formed in the side walls 321, which can be sterile sealed by a protective foil, such as a meshwork of synthetic fibers such as polypropylene fibers (PP) or a Tyvek® protective foil.

A plurality of pins 324 project perpendicularly from the bottom 323 of the upper segment 320, which act as positioning devices (positioning means) in the sense of the present application, which are arranged in a regular array and which form respective receptacles 325, in which the containers, such as vials, can be accommodated (cf. FIG. 1c).

FIG. 1b shows a matching lower segment 330 that is also formed in the manner of a drawer having a bottom 333, two lateral side walls 331 and a rear side wall 332, both of which protrude at right angles from the bottom 333.

The two segments 320, 330 may be inserted in the manner of drawers, as shown in FIG. 1c, to jointly form a transport and packaging container 1, in which the containers 2 are accommodated in a regular array and sealed against the environment, The containers 2 can be placed upright or upside down in the receptacles formed by the pins 324. The bottoms of the containers 2 can thereby be supported directly on the bottom 333 of the upper segment 320.

The two segments 320, 330 together with the containers positioned by one of the two segments can be inserted into each other. Further measures to seal the transport and packaging container 1 will be described below with reference to FIGS. 4a-4d.

Figure 2B:
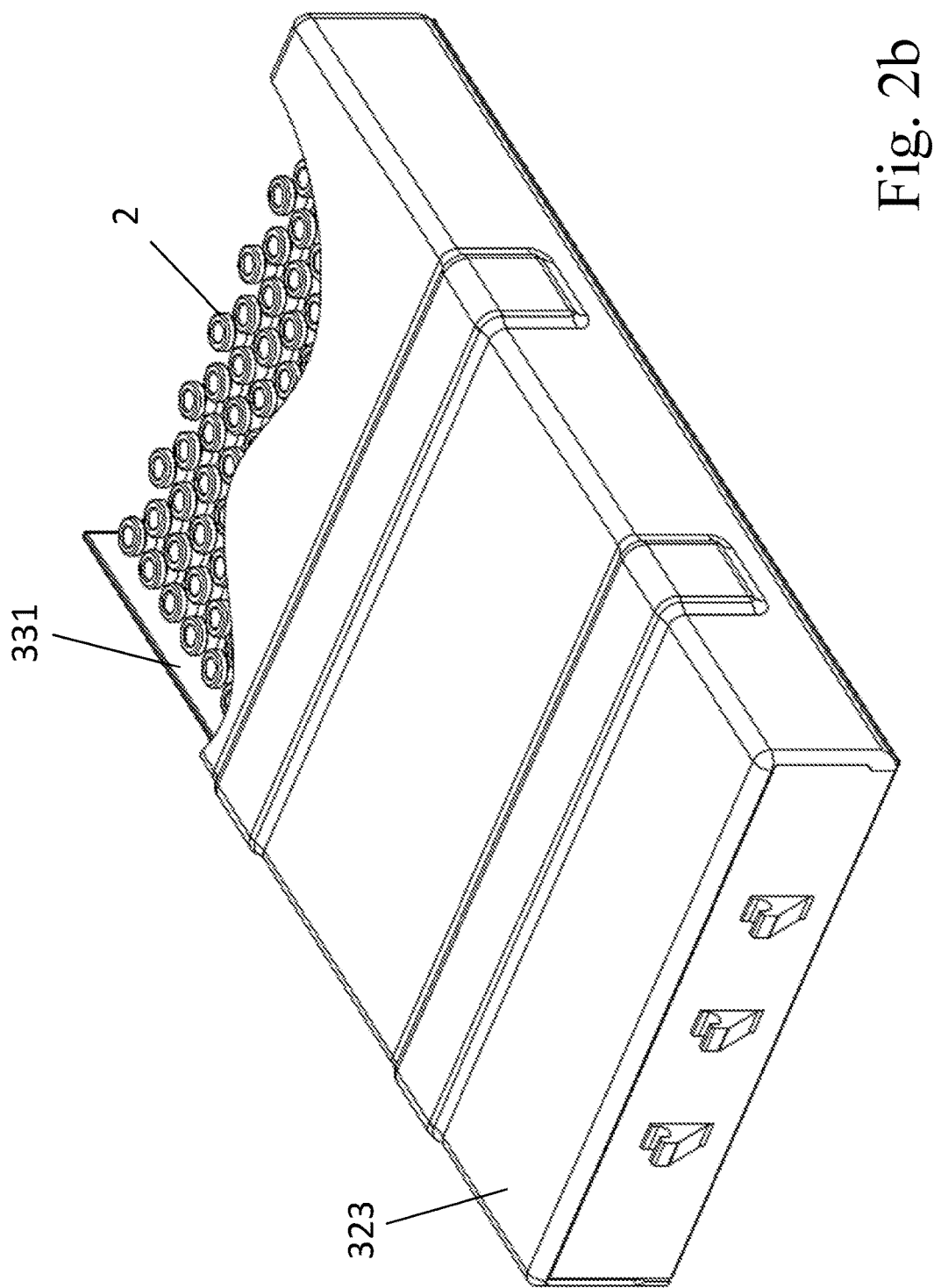

FIGS. 2a and 2b show a further embodiment of such a transport and packaging container 1.

FIG. 3 shows a further embodiment for a transport and packaging container 1, in which the bottom 323 of the upper segment is formed with a mesh-like structure formed of intersecting plastic webs 326 and perforations, through which a gas can flow to sterilize the interior of the transport and packaging container 1. The transport and packaging container 1 is sealed by a sterile protective foil 130, as described above. The protective foil my also cover the circular openings 329.

FIGS. 4a to 4d show further details of the two drawer-like segments 320, 330 of the transport and packaging container. According to the enlarged view of the area A in FIG. 4d, a rectangular guide rail 335 is formed on the side wall 331 of the upper segment, which extends in the longitudinal direction, is formed as a protrusion and faces the associated side wall 321 of the lower segment 320 (see FIG. 4b). According to the enlarged view of area B in FIG. 4c a corresponding rectangular-shaped recess 327 is formed on the side wall 321 of the lower segment, which extends in the longitudinal direction to accommodate and guide the guide rail 335. Already due to the design of the recess 327 and of the guide rail 335 a sealing of the interior of the transport and packaging container is accomplished.

This sealing may be assisted by additional sealing means, which are formed along the lower segment of the two segments, as shown schematically in FIGS. 4c and 4d. According to FIG. 4c, a rectangular protrusion 328 is formed along the bottom edge of the side wall 321 of the lower segment, which extends in the longitudinal direction. According to FIG. 4d a rectangular recess 336 is formed along the bottom edge of the side wall 331 of the upper segment, which extends in the longitudinal direction. Protrusion 328 and recess 336 are formed corresponding to each other and can be brought into a mutual engagement when inserting the two drawer-type segments, whereby a further sealing effect is achieved in this area.

Referring to FIGS. 4c and 4d a distance Δh is formed between the recesses and protrusions 327, 328 and 336, 335, respectively, which is in each case identical. On the surfaces of the recesses and protrusions 327, 328 and 336, 335, respectively, a plastic coating or a sealing lip (not shown) may be provided to enable an additional sealing effect in this area. This sealing function can be enhanced further by the resilient characteristics of such a plastic coating or sealing lip.

Figure 4A:
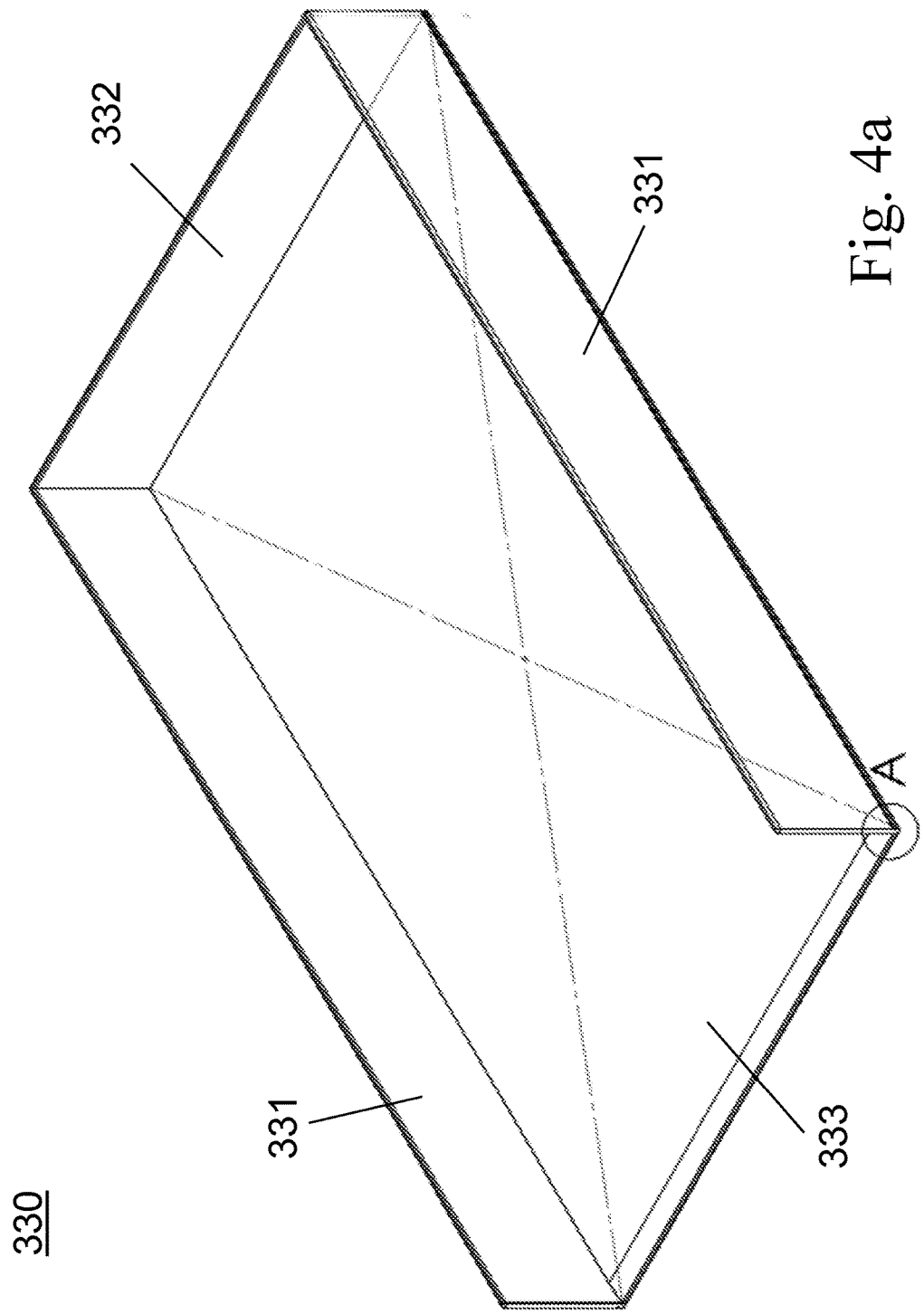
Figure 4B:
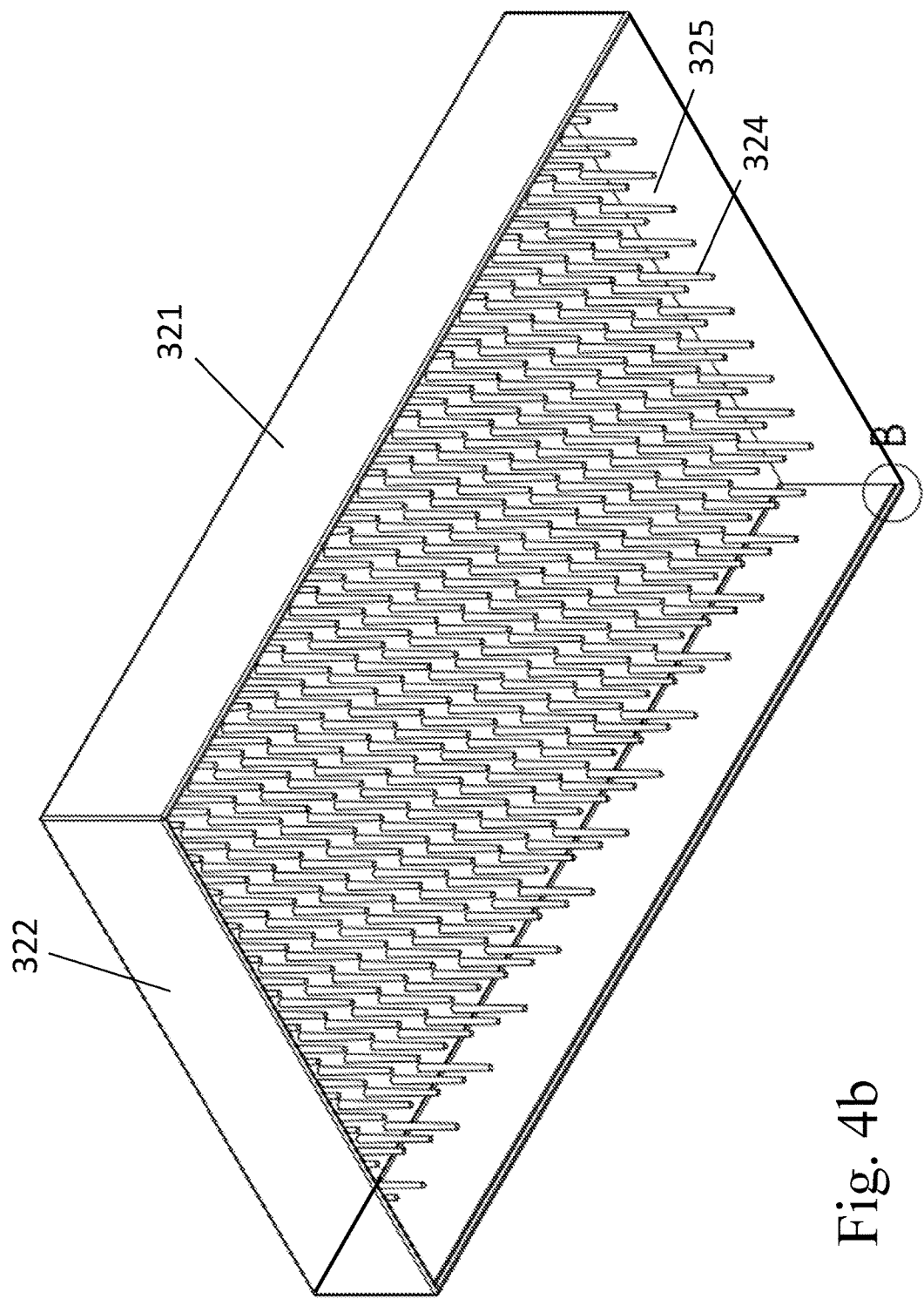

According to FIG. 4a similar measures for sealing the interior of the transport and packaging container are provided also on the front edge 333 of the upper segment 330. For this purpose, a recess or a protrusion may be formed along the front edge 333, which cooperates with a correspondingly shaped protrusion or a correspondingly shaped recess to provide a sealing effect in this area. Of course, also in this area an additional plastic coating or sealing lip (not shown) may be provided, as described above.

In the arrangements described above, the containers 2 are arranged in a regular arrangement distributed along two mutually orthogonal directions and in a plane at predetermined constant intervals. In principle also other periodic arrangements are conceivable: for example, adjacent rows or columns of containers 2 may also be offset by a predetermined length from one another, namely in a periodic configuration with a predetermined periodicity. Thus, automated production systems may expect the containers 2 at precise predetermined positions when they are transferred to a processing station, which significantly reduces the automation effort necessary. The further processing of the containers 2 can be performed while they are accommodated in a supporting structure 25 and/or while the containers are accommodated in one of the segments of the transport and packaging container.

For this purpose, it is expedient if the bottom of the transport and packaging container is formed of a metal, wherein the metal is advantageously coated with a plastic material, in particular a thermoplastic, which resists temperatures of up to 330° C. and more preferably of up to 350° C., in particular, polyimide (PI) having a melting point of about 368° C., polyetherketone (PEK) having a melting point of about 375° C., polyetheretherketone (PEEK) having a melting point of about 341° C., polyetherketoneketone (PEKK) having a melting point of about 380° C. or polyetherketoneetherketoneketone (PEKEEK) having a melting point of about 384° C.

For this purpose, it may also be expedient if the bottom of the transport and packaging container is formed of a high-temperature-resistant plastic material, in particular of a thermoplastic or polyimdide (PI) or polyetherketone (PEK) or of polysulfone (PSU) or of polyetheretherketone (PEEK), or preferably of a polyetheretherketon (PEEK) having a melting point above 330° C., more preferably up to 350° C.

FIGS. 6a to 6e show a further embodiment of a supporting structure (carrier). This supporting structure 25 is formed by a plurality of hexagonal receptacles 39 for accommodating containers 2, which are formed by two pairs of side walls 45 converging at an obtuse angle which are connected with each other via flexible clamping webs 46. As can be concluded from FIG. 6b, each of the flexible clamping webs 46 comprises a concave holding portion 46a, wherein the connecting webs 47 are formed mirror-symmetrically, so that the concave indentations on both sides of the clamping webs 46 face the side walls of the associated containers 2. At the lower end of the supporting receptacles 39 wave-shaped webs 47 connect the two clamping webs 46a with each other. The webs 47 may be used as supporting webs for supporting the containers 2 accommodated in the receptacles 39. As an alternative, the webs 47, may bias respective opposite side walls of the receptacles 39 elastically towards each other so that containers with different diameters can be clamped easily. The supporting structure 25 according to FIG. 6a can in principle be injection molded as one piece from a plastic.

The wave-shaped webs 47 press the receptacles 39 of the supporting structure 25 in the illustration of FIG. 6a laterally apart, so that the clamping webs 46 with their indentations 46a are pressed against the circumferential sidewalls of the containers 2 in the first position shown in FIG. 6c so that the containers 2 are accommodated with sufficient holding forces in the receptacles 39, as shown in the insert according to FIG. 6b. For transferring this supporting structure 25 starting from the position shown in FIG. 6b into the second position shown in FIG. 6c in which the clamping webs 46 with their indentations 46a do not clamp anymore the circumferential side walls of the containers 2 or at best only with a small force, so that the containers may be removed from the receptacles without much effort or so that they can be displaced therein, the supporting structure 25 must be pulled apart in transverse direction in the illustration of FIG. 6a. For this purpose, form-fitting elements 48 having an L-shaped profile are formed on the outer walls of the outermost hexagonal receptacles 39, which form T-shaped receptacles, into which a correspondingly shaped latching rail 49 is inserted. By pulling these latching rails in the transverse direction, the supporting structure can be spread and at the same time all receptacles 39 can be expanded. Depending on how much one pulls laterally at the latching rails 49, the receptacles 39 can be expanded suitably. Thus, by compression of the receptacles 39 overall the opening widths of the receptacles 39 may be transferred in a coordinated manner from the first position according to FIG. 6c to the second position according to FIG. 6b, in which the containers 2 are fixed at predetermined positions by friction.

The height level of the containers 2 is here defined essentially by the webs 47 because the bottoms of the containers 2 are supported on the webs 47. As can be concluded from the sectional view of FIG. 6e, the majority of the bottoms of the containers 2 is freely accessible from below, for example, for a mechanical adjusting device.

Figure 7A:
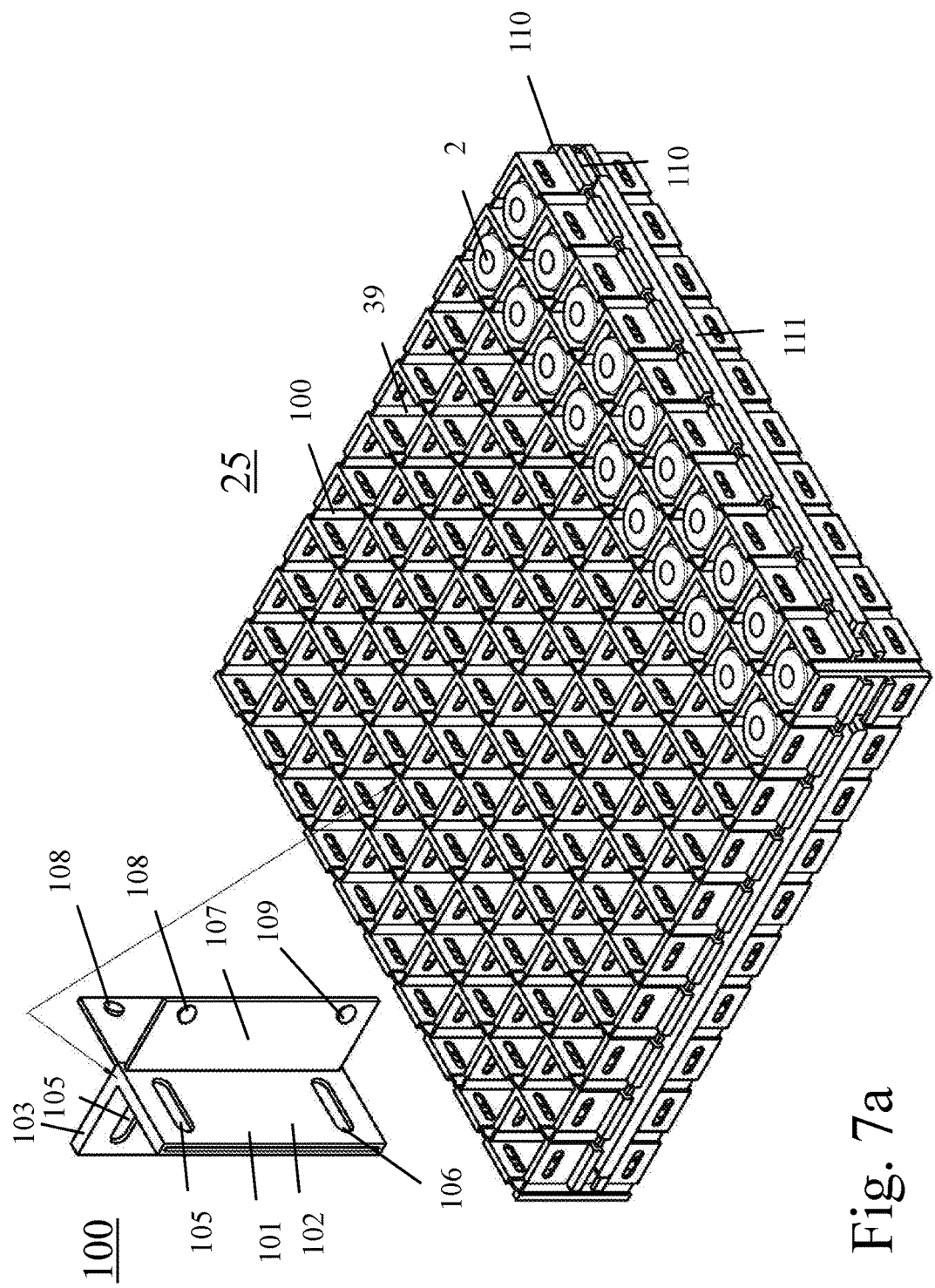
Figure 7B:
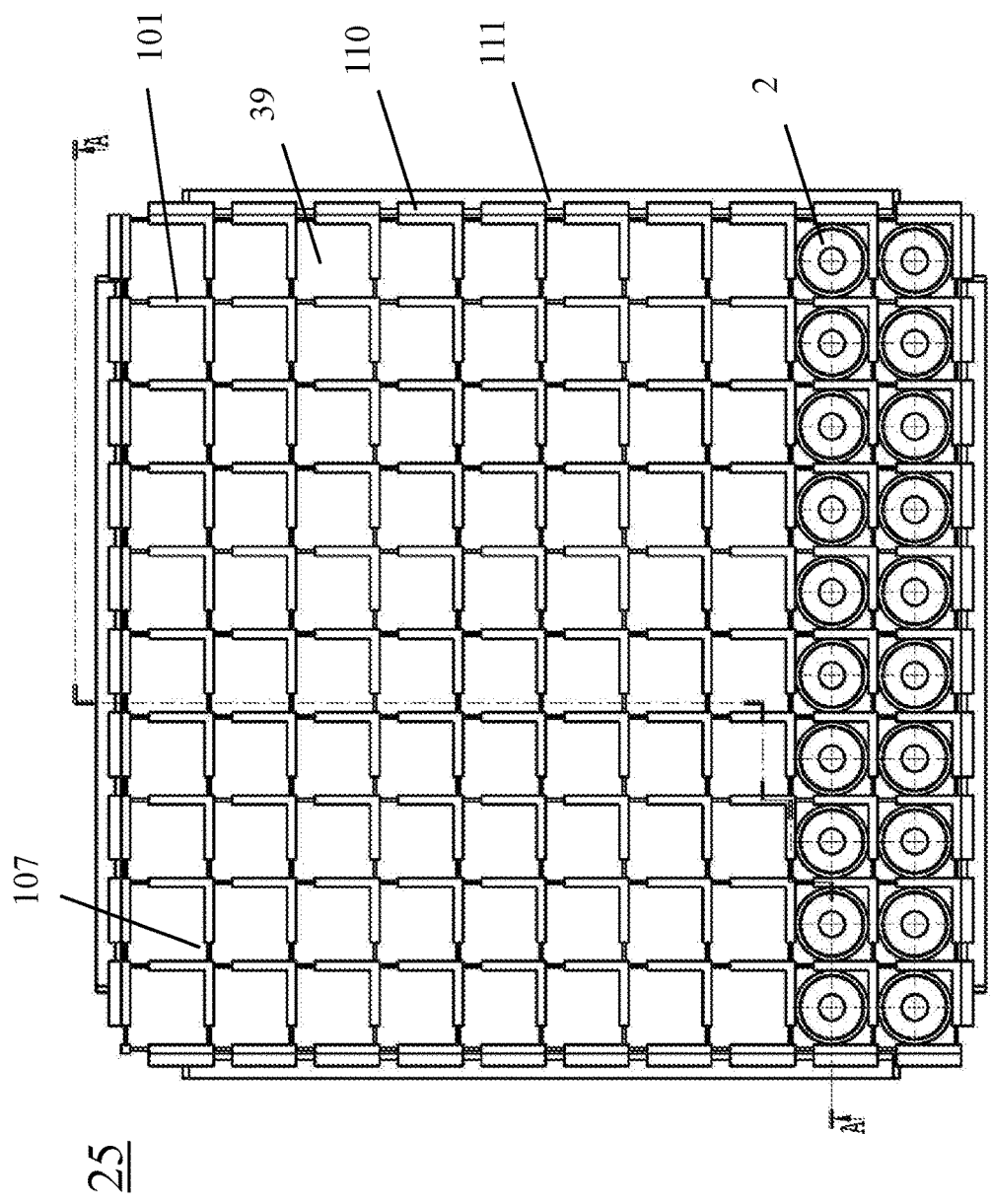
Figure 7C:
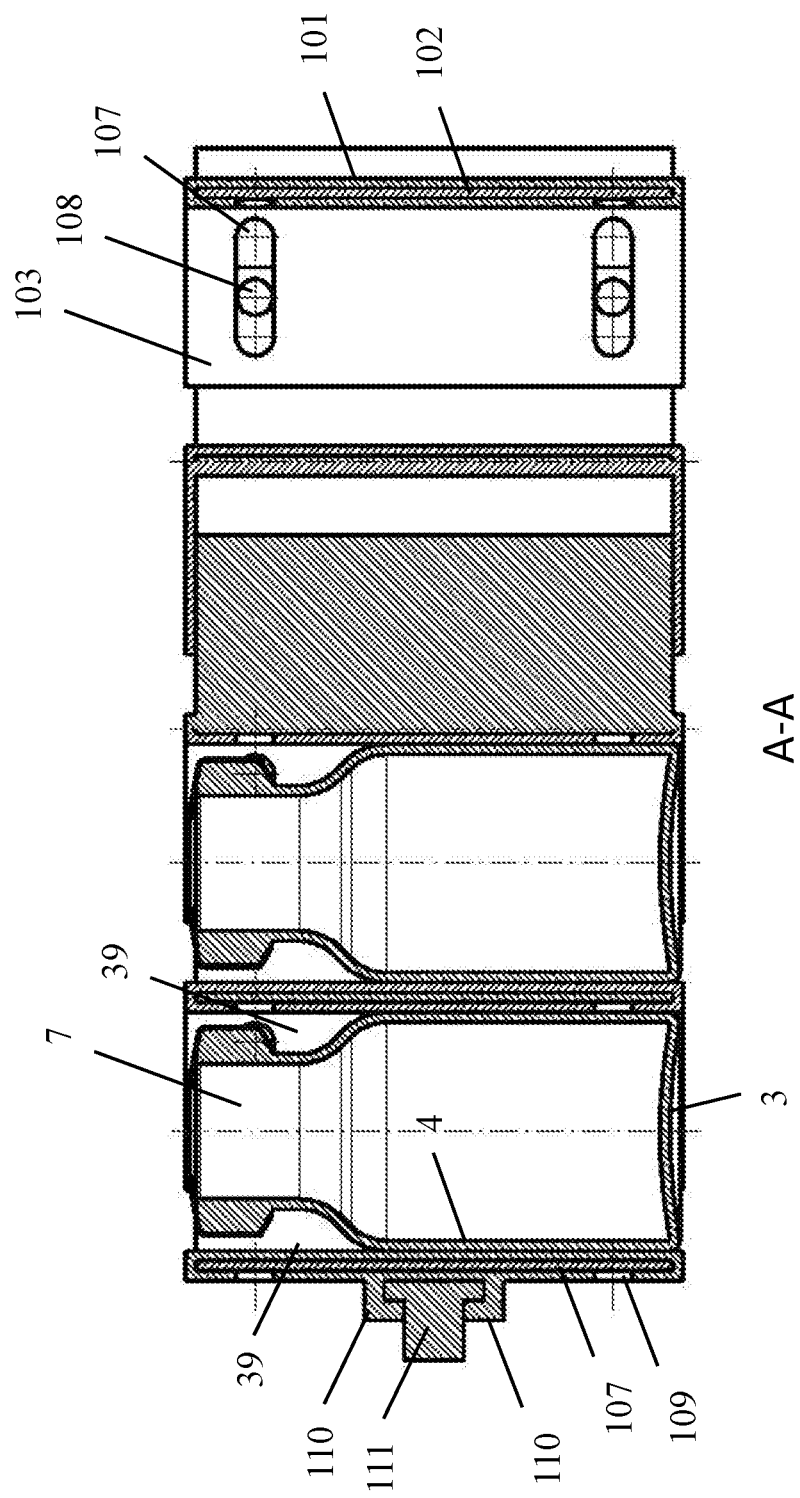

FIGS. 7a-7c show a further example for a supporting structure for use in a transport and packaging container according to the present disclosure. According to the upper part of FIG. 7a, this supporting structure 25 comprises side walls 101, 103, 107 which have identical leg lengths and intersect each other perpendicularly. Two of the side walls, namely the side walls 101, 103, are slit, having a longitudinal slot 102, which extends substantially over the entire height of the side walls 101, 103. An upper long hole 105 and a lower long hole 106 extending in parallel with each other are formed in the side walls 101, 103. The thickness of the side walls 107 is matched to the width of the longitudinal slot 102 such that they can be accommodated therein. Cylindrical protrusions 108, 109 are formed on the side walls 107, which are guided in the upper and lower long hole 105, 106, when the side walls 107 are inserted in the associated longitudinal slot 102. A plurality of such base units 100 is stuck together to a rectangular supporting structure 25, as shown in the lower right-hand part of FIG. 7a.

FIG. 7b shows the supporting structure 25 according to FIG. 7a in a schematic plan view. The side walls 101 of the base units serve as guide plates for the latching plates 107 of the base units accommodated therein. Because of the co-operation of the protrusions 108, 109 with the associated long holes 105, 106, the base units are mounted displaceably in the plane of the supporting structure 25. Because of the co-operation of the base units thus a plurality of substantially square-shaped or rectangular elongated receptacles 39 are formed, into which the containers 2 can be inserted from above or from below. For insertion of the containers, the base units are spread apart such that the opening widths of the receptacles 39 allow an unimpeded insertion of the containers or at least an insertion of the containers with minimum force. Then all the base units can be pressed against each another in a coordinated manner so that the containers 2 accommodated in the receptacles 39 are finally fixed, in particular clamped, with sufficient frictional force. FIG. 7c shows the supporting structure 25 according to FIG. 7b in a partial longitudinal section along line A-A of FIG. 7b.

In this embodiment the rectangular basic shape of the supporting structure 25 is achieved by the form-fitting elements 110 having an L-shaped profile, which are disposed on the outer walls of the outer base units, so that an essentially U-shaped receptacle having a longitudinal slot is formed in the base, into which the latching rail 111 is engaged, which is provided with a corresponding T-shaped profile. By means of the latching rail 111 also a fixation of the positions of all the base units 100 may be accomplished, for example by screwing or clamping of the latching rail 111 in any case to the front and rear base units 100 of a column or row of the matrix-shaped supporting structure 25.

FIGS. 8a-8d show a further example for a supporting structure for use in a transport and packaging container according to the present disclosure. This supporting structure 25 comprises a plurality of transverse webs 35, which extend in parallel with each other and which are connected to each other via S-shaped connecting webs 36, which are disposed at regular intervals and extend substantially perpendicularly to the transverse webs 35. More specifically, the connecting webs 36 are connected with the transverse webs 35 via front and rear ends 37, 38, respectively, which are curved over in opposite directions. The connecting webs 36 are made of a plastic, preferably from a flexible plastic. The transverse webs 35 preferably have a greater stiffness than the connecting webs 36. Due to the S-like shape of the connecting webs 36, the transverse webs 35 are offset to each to each other in the longitudinal direction by a constant distance, so that the supporting structure 25 is configured overall as a parallelogram having a basis in the region of the lower rim of the supporting structure 25 shown in FIG. 8a and two imaginary lines extending at an acute angle, which connect the front ends of the transverse webs 35 with each other. In the relaxed home position shown in the right-hand part of FIG. 8a the containers 2 can be inserted into the elongated holding receptacles 39 formed by the webs 35, 36 freely and without contact with the webs 35, 36, or at least with minimal forces. The supporting receptacles 39 have essentially a square-shaped cross section which is matched to the diameter of the containers 2 such that these may be fixed therein, and in particular can be clamped therein, with a sufficient frictional force in a second position of the supporting structure 25.

Figure 8B:
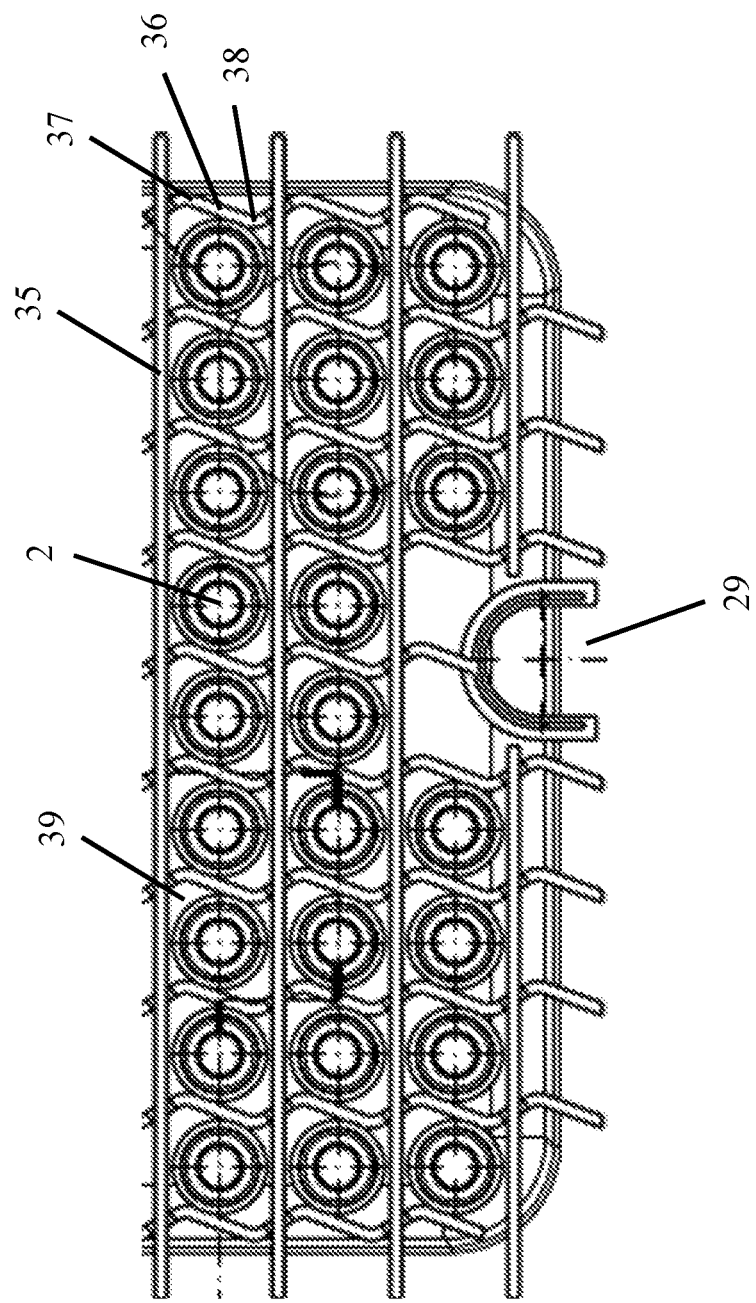

For converting the supporting structure 25 from the first position shown in FIG. 8a into the second position shown in FIG. 8b, the transverse webs 35 may be shifted respectively in their longitudinal direction so that, finally, the square-shaped or quadratic supporting structure 25 shown in FIG. 8b is formed. As can be derived from the comparison of FIGS. 8a and 8b, the connecting webs 36 are slightly bended for this purpose. To this end, all side walls of the receptacles 39 are adjusted in a coordinated manner, i.e. jointly, from the first position to the second position upon displacement of the transverse webs 35, namely by pivoting the upper end of the supporting structure (cf. FIG. 8a) relative to the basis at the lower end of the parallelogram shown in FIG. 8a.

Figure 8D:
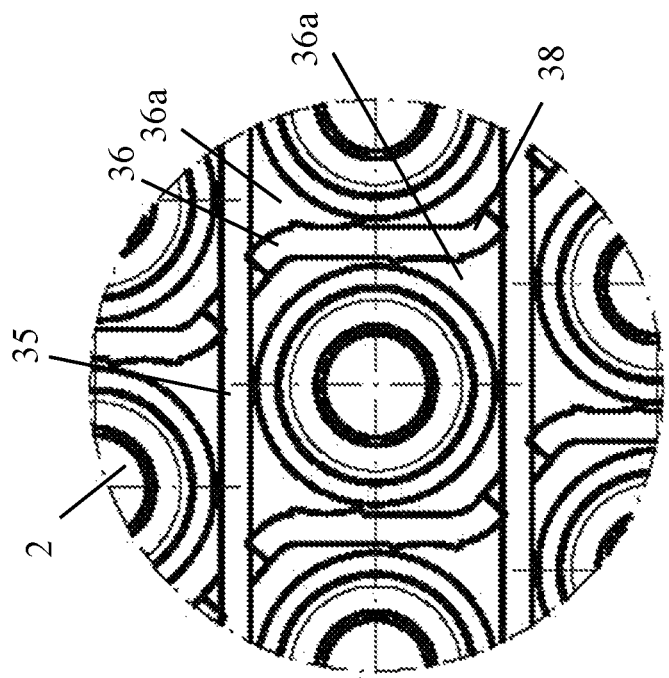
Figure 8C:
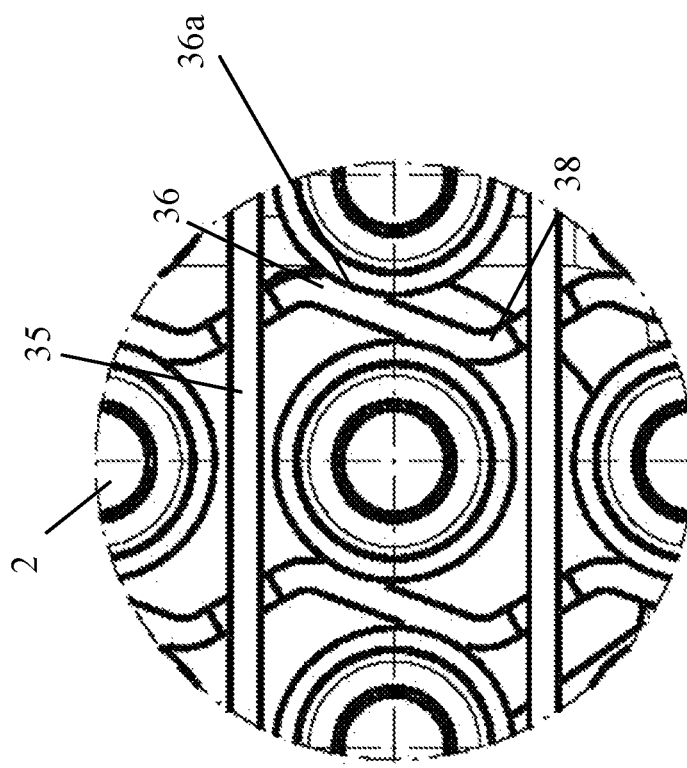

FIGS. 8c and 8d show in greatly enlarged partial views the fixation of the containers 2 at such a supporting structure. On both sides of the supporting webs 36 respective concave portions 36a are formed, wherein the radius of curvature of both concave receptacles of the portions 36a is matched to the radius of the containers 2. In the second position according to FIG. 8c, in which the connecting webs 36 extend inclined relative to the transverse webs 35, the concave receptacles 36a nestle to the cylindrical side walls of the containers 2, so that the containers can be held more reliably and more precisely. In the first position according to FIG. 8d, in which the connecting webs 36 extend perpendicular to the transverse webs 35, the concave receptacles 36a are not disposed anymore opposite to the cylindrical side walls of the containers 2 so that the containers may be inserted into the receptacles formed by the webs 35, 36 without hindrance, or at least with a significantly reduced force, and removed therefrom. Ideally, the webs 35, 36 do not abut to the side walls of the containers 2 in the first position according to FIG. 8d.

While it was explained in the previous embodiments, that the containers are placed upright and with its open end toward the upper end of the transport and packaging container, the containers can in principle also be reversed, i.e. with their open end pointing toward the bottom of the transport and packaging container.

Figure 5C:
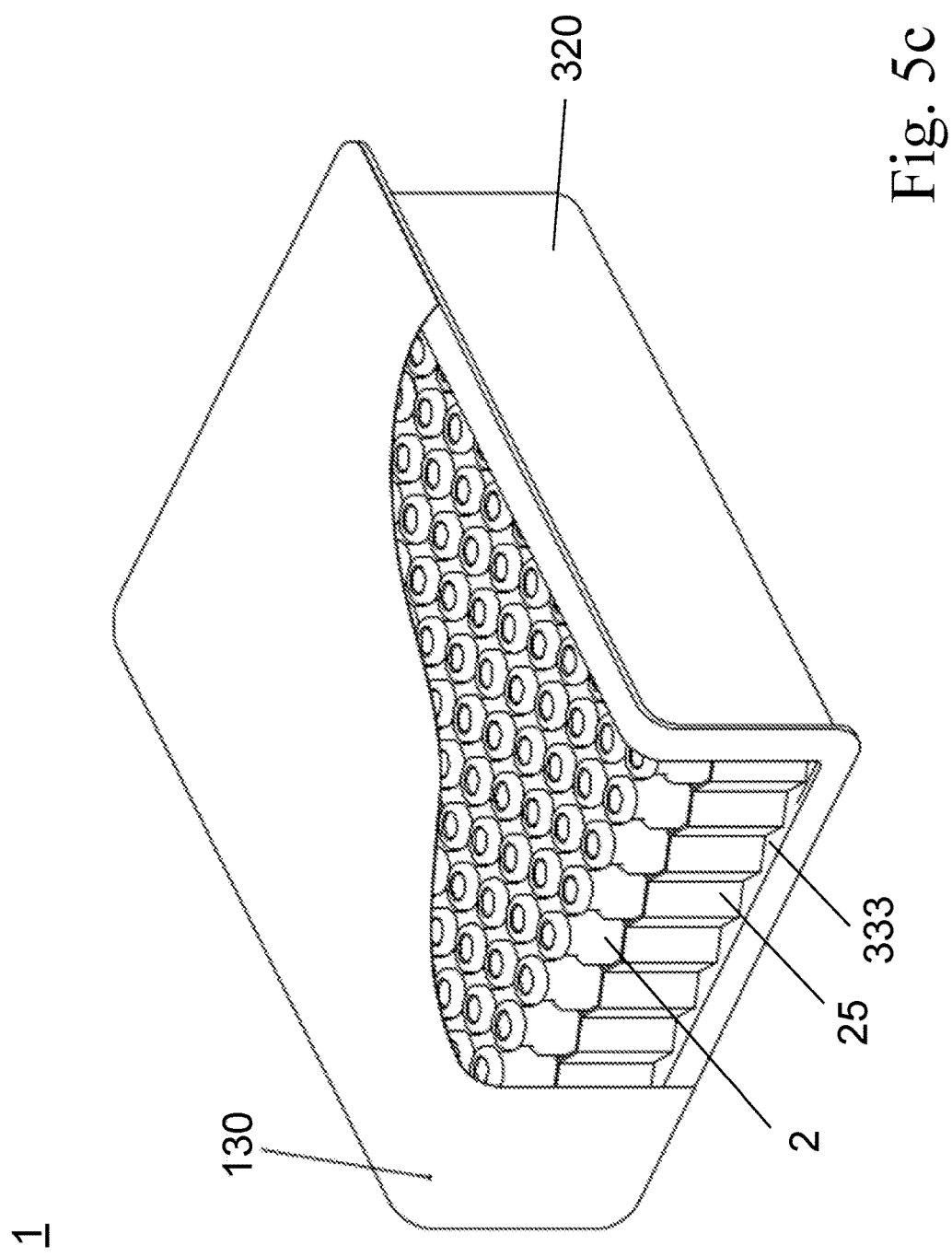

The upper side or the upper side and bottom side of a supporting structure 25 according to the present disclosure or also of a transport and packaging container 1 according to the present disclosure can be covered by a sterile, gas-permeable protective foil which is bonded and drawn off, if necessary. This is exemplified in FIG. 5c, where the foil 130 is bonded on the upper rim of the lower segment 320. The protective foil can in particular be a gas-permeable plastic foil, in particular a meshwork of synthetic fibers, such as polypropylene fibers (PP) or a Tyvek® protective foil, which enables the sterilization of containers accommodated and packaged in the supporting structure 25 by means of a gas that flows through the film 130 into the interior of the transport and packaging container 1.

Figure 9:
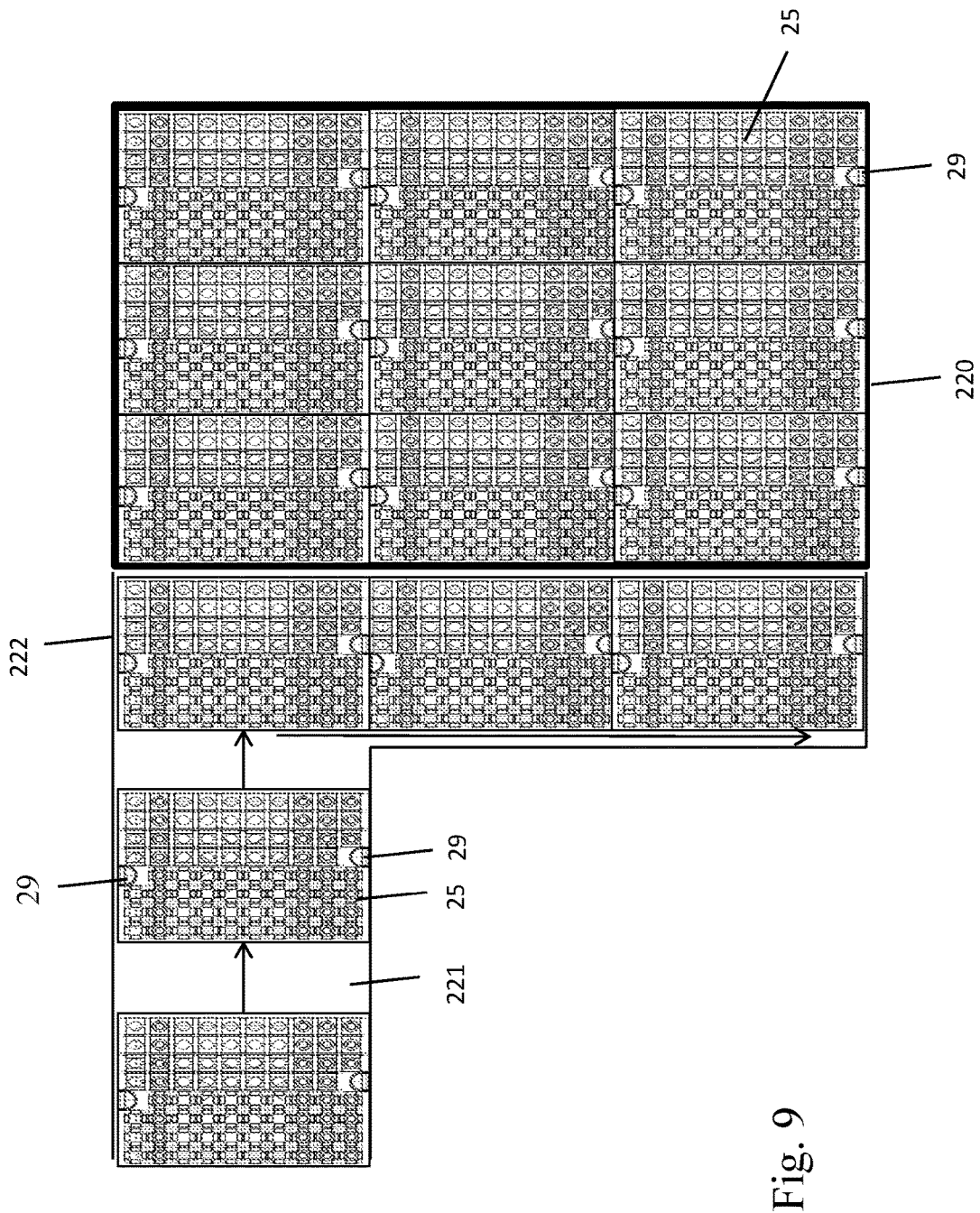
FIGS. 9-10 show examples of processes according to the present disclosure in which containers for substances for medical or pharmaceutical applications are processed at very high temperatures while they are accommodated in a carrier.

FIG. 9 schematically shows a schematic top view of a process in which a plurality of containers are processed at very high temperatures, for example in a thermal processing station, in particular in a hot oven or a hot tunnel, with temperatures of up to 330° C. and preferably of up to 350° C., while the containers are supported in a carrier 25 and in a regular array configuration, as described above.

According to FIG. 9, the carriers 25 together with the containers supported by the carrier 25 in a regular two-dimensional arrangement are conveyed by means of the conveyor 221, such as a conveyor belt or a roller conveyor, in the direction of the arrow toward a hot oven or hot tunnel 220. This can for example be arranged laterally to a main conveyor of a processing plant, not shown, where the carrier 25 is transferred or passed onto the conveyor 221 and conveyed toward a hot oven or hot tunnel 220. Upstream from the hot oven or hot tunnel 220 a supporting surface or shelf is provided, which extends transversely to the conveyor 221 and on which the carriers are collected. This collection of the carriers 25 upstream from the hot oven or hot tunnel 220 may also be effected at several levels, in correspondence to the levels of the hot oven or hot tunnel 220.

Figure 10:
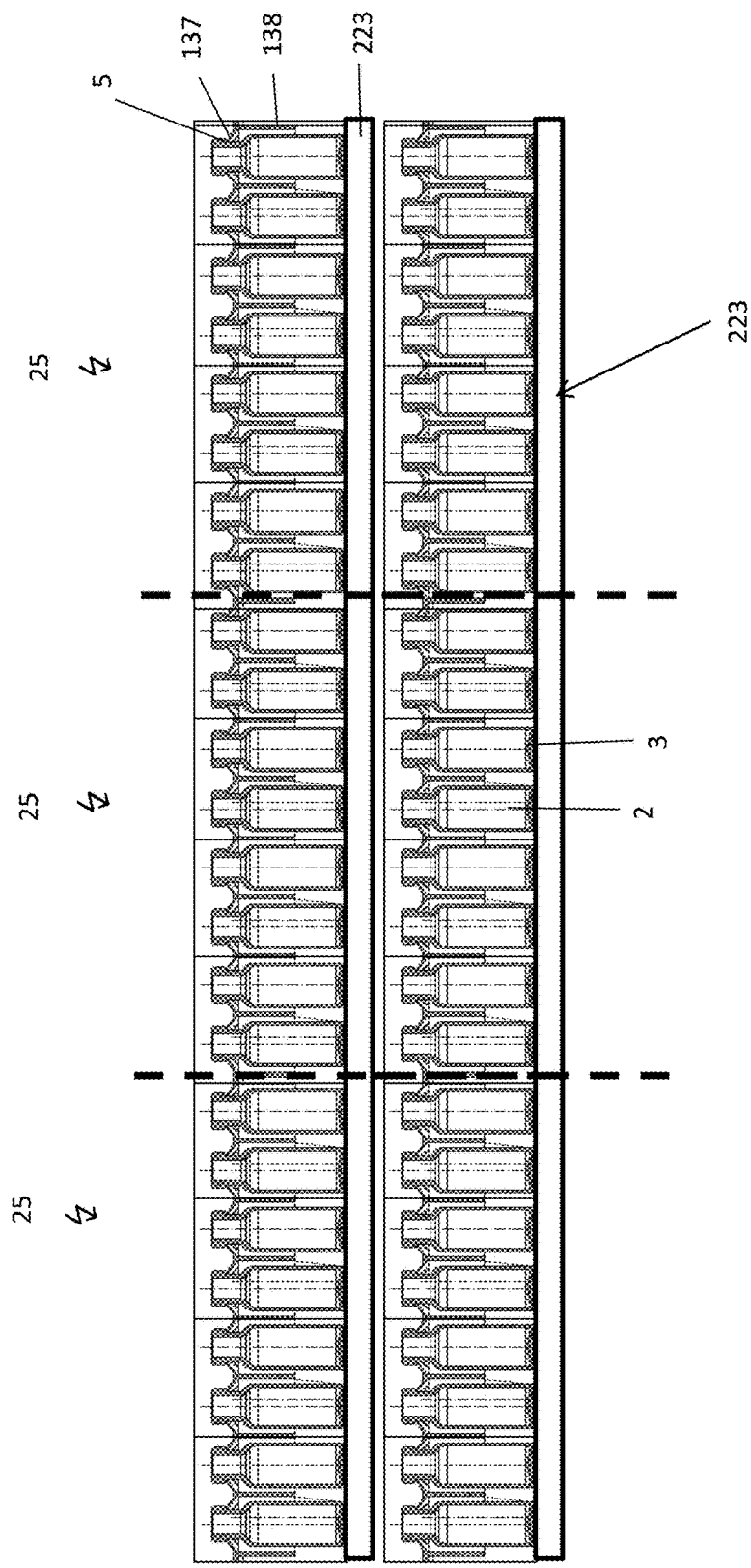

In order to reduce the base area of the carrier 25 even further, it may be advantageous if the edge portions 150 of the carrier 25 can be removed or pivoted away. This simple measure increases the achievable packing density of the container 2 when loading the hot oven or hot tunnel 220. FIG. 10 shows an enlarged partial section through a freeze-dryer. As can be seen, the bottoms 3 of the containers 2 rest directly on the trays 223 at very high temperatures, so that an optimum and rapid heating of the containers 2 can be accomplished, in particular of their bottoms and bottom portions. Here, the bottoms 223 are arranged on several levels.

For processing the containers 2 at the very high temperatures, it is not necessary to remove them out of the carriers and isolate them, which would be awkward. Rather, the containers 25 are still accommodated reliably in the receptacles of the carrier 25 during processing. To ensure the thermal stability of the carrier 25, the carrier 25 and/or at least the receptacles of the carrier 25 are formed of a high-temperature-resistant plastics material, in particular of a thermoplastic, which can withstand to the high processing temperatures of up to 330° C. and preferably up to 350° C. Preferably the thermoplastic is polyimide (PI), polyetherketone (PEK), polyetheretherketone (PEEK), polyetherketoneketone (PEKK) or polyetherketoneetherketoneketone (PEKEEK) having a melting point of up to 330° C. and preferably up to 350° C.

The processing of the plurality of containers 2 in the hot oven or hot tunnel at tem-temperatures of up to 330° C. and preferably up to 350° C. is performed in such a manner that endotoxins and/or the lysis of bacteria and/or cytokine inducing substances in the containers 2 can be removed thermally.

The processing of the plurality of containers 2 in the hot oven or hot tunnel at tem-temperatures of up to 330° C. and preferably up to 350° C. can also be performed in such a manner that silicon layers on inner surfaces of the containers 2, and in particular on a bottom 3 and bottom portion thereof, are burnt-in. Applying the silicon layer (siliconization) is performed by applying an amount of silicone oil or emulsion on at least a portion of the inner surface of each container. For this purpose a predetermined amount of silicone may be applied. In addition, it can be provided to remove excess silicone immediately, for example by wiping or rinsing. The deposited silicone oil is then fixed or baked by heat treatment at temperatures between 150° C. and 350° C. For this purpose it may be further provided that unbound or non-covalently bound silicone is removed completely or partially by wiping or rinsing.

Of course, the aforementioned processing of the containers does not rule out that these are e.g. displaced temporarily by lifting to a different level. This can be achieved for example by means of a coordinated adjustment of all receptacles 39 of the carrier 25, as shown for example in FIG. 8a. In this position, the levels or height positions of the containers 2 can be adjusted while they are still disposed in the receptacles 39 of the carrier or at least guided therein.

According to an alternative embodiment (not shown), the containers are processed in the hot oven or hot tunnel at the very high temperatures of up to 330° C. and preferably up to 350° C. while they are accommodated in a transport and packaging container, as described above and while they are positioned reliably by the positioning devices in the array configuration. To ensure the thermal stability of the transport and packaging container and of its positioning devices, the transport and packaging container, or at least its bottom portion, which may be formed by one segment, as described above, is formed of a high-temperature-resistant plastic material, in particular of a thermoplastic that can withstand temperatures of up to 330° C. and more preferably up to 350° C., in particular of polyimide (PI), polyetherketone (PEK), polyetheretherketone (PEEK), polyetherketoneketone (PEKK) or polyetherketoneetherketoneketone (PEKEEK).

According to an alternative embodiment the transport and packaging container, or at least its bottom portion, is formed of a metal that can withstand the temperatures during the processing of up to 330° C. and preferably up to 350° C.

For the processing the transport and packaging container can be opened first, as described above, by shifting or releasing at least one segment of the plurality of segments 320, 330 (see FIG. 1c, 2a or 3) or of the transport and packaging container in such a way that the interior of the transport and packaging container is accessible to let, for example, a gas flow into the interior.

In this open state, or alternatively, while the transport and packaging container is closed, the processing in the hot oven or hot tunnel is performed at the very high temperatures of up to 330° C. and preferably up to 350° C., while the containers are positioned in the regular array configuration by the positioning devices or by a carrier disposed in the transport and packaging container.

If the transport and packaging container has been opened for the processing, the assembling or sticking together of the segments for closing again the transport and packaging container is performed in such a manner that the sealing means seal the interior of the transport and packaging container sterile against the environment.

Figure 11:
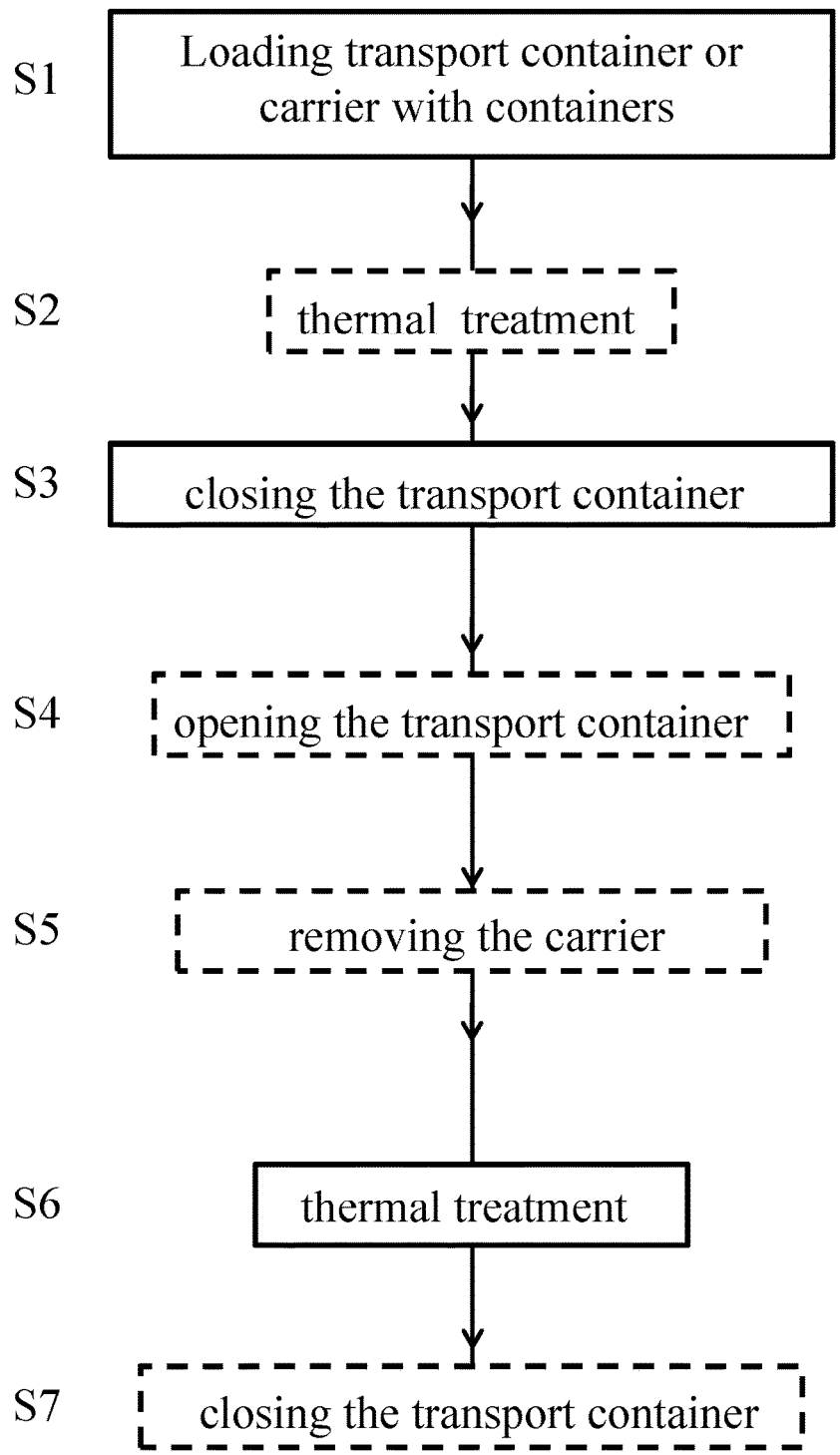
FIG. 11 shows a schematic flow diagram of a process according to the present disclosure, as shown in FIGS. 9 and 10.

Referring to the schematic flow diagram of FIG. 11, a process according to the present disclosure is described by way of example. In FIG. 11 the blocks framed by dashed lines denote process steps that can be performed optionally, depending on the specific embodiment.

Figure 6D:
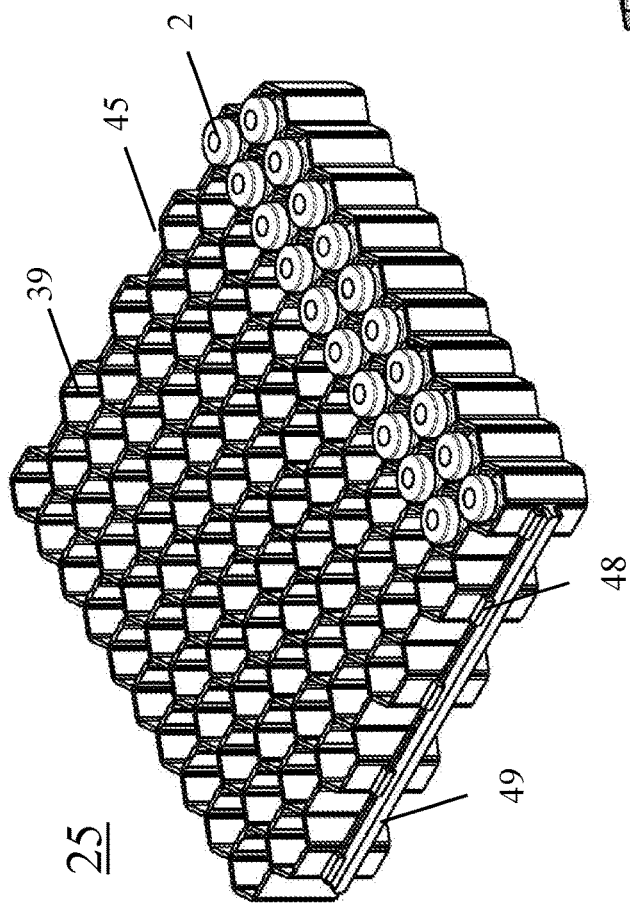
FIGS. 6a-8d show further supporting structures, which are suitable for use in a transport and packaging container according to the present disclosure.
Figure 6E:
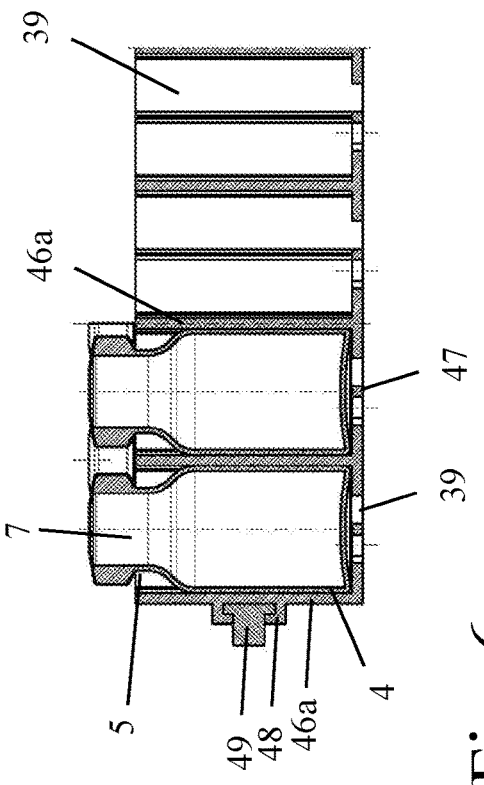

In step S1, the transport and packaging container (in FIG. 11 simply referred to as transport container) is loaded with containers, for example by inserting the containers into the receptacles 325 formed by the positioning devices 324 of FIG. 1a; or the carrier is loaded with containers, for example with vials or cartridges, as exemplified in FIG. 6d. Then in step S2 a pretreatment of the transport container may be performed, for example a sterilization of the transport container. In step S3, the transport container is closed, in which the containers are either accommodated directly or in which a carrier is accommodated which in turn accommodates the containers, as described above. In this state, the containers are accommodated in the transport container sterile and reliably positioned and can for example be stored or shipped to a pharmaceutical company.

In the optional step S4, the transport container can be opened again to provide access to the containers accommodated therein or to the carrier accommodated therein. Unless the thermal treatment of the containers should not be carried out directly in the transport container, the optional method step S5 follows, in which the carrier is removed from the transport container.

Then, in step S6 a thermal treatment of the containers is performed, either while they are accommodated in the preferably closed transport container or while they are accommodated in the carrier after the carrier has been removed out of the transport container. The thermal treatment can in particular take place at very high temperatures of up to 330° C. and preferably up to 350° C.

Then, the containers can be processed either immediately, e.g. they can be filled and then sealed sterile and packaged, or they are inserted together with the carrier again into the transport container, which is then sealed again in the optional process step S7, as described above. In the latter state, the heat treated containers can then be sterile stored or transported in the transport container.

It will be readily apparent for the person skilled in the art upon reading the above description that the various aspects and features of the embodiments described above may be combined in any manner with one another, resulting in numerous further embodiments and modifications. It will be readily apparent for the person skilled in the art upon reading the above description that all such further embodiments and modifications shall be comprised by the present disclosure, as long as these do not depart from the general solution and scope of the present disclosure, as defined in the appended claims.

What is claimed is:

1. A transport and packaging container for accommodating a plurality of cylindrical containers for substances for medical, pharmaceutical or cosmetic applications, comprising:
   a first segment having a bottom and a plurality of upright side walls protruding perpendicularly from the bottom; and
   positioning devices for positioning the containers in interior of the transport and packaging container in a regular arrangement in such a manner that a collision of directly adjacent containers is prevented; wherein
   an upper end of the first segment opposite to the bottom and a side of the first segment are open to enable removal of the containers via the upper end or an open side of the first segment,
   the upper end of the first segment and the open side of the first segment are covered by a protective foil so that the interior of the transport and packaging container is sterile sealed against the environment, wherein the first segment is formed like a drawer having three upright side walls protruding perpendicularly from the bottom, and wherein the protective foil is bonded to rims of the first segment for covering the upper end of the first segment and the open side of the first segment.

2. The transport and packaging container according to claim 1, wherein the protective foil is a gas-permeable plastic foil.

3. The transport and packaging container according to claim 2, wherein the gas-permeable plastic foil is a meshwork of synthetic fiber.

4. The transport and packaging container according to claim 1, wherein the positioning devices are formed directly on the bottom of the first segment.

5. The transport and packaging container according to claim 4, wherein the positioning devices are formed as a plurality of pins projecting perpendicularly from the bottom of the first segment, wherein the plurality of pins is arranged in a regular array to form respective receptacles, in which the containers can be accommodated in the regular arrangement.

6. The transport and packaging container according to claim 1, wherein the positioning devices are formed by a plurality of receptacles, which are formed in a carrier that can be inserted into and removed out of the transport and packaging container, the carrier being configured such that the containers can be inserted into associated receptacles, wherein the receptacles extend in a longitudinal direction of the containers and are configured to support sidewall portions of the containers at least partially clamped.

7. The transport and packaging container according to claim 6, wherein the receptacles are formed by continuous side walls and wherein opening widths of the receptacles can be adjusted by a coordinated adjustment of the side walls between a first position, in which the containers can be inserted into the receptacles, and a second position, in which the containers are clamped.

8. The transport and packaging container according to claim 7, wherein the receptacles are formed as hexagonal receptacles for accommodating the containers, wherein the hexagonal receptacles are formed by two pairs of side walls converging at an obtuse angle which are connected with each other via flexible clamping webs.

9. The transport and packaging container according to claim 8, wherein each of the flexible clamping webs comprises a concave holding portion, wherein connecting webs are formed mirror-symmetrically, so that concave indentations formed on both sides of the clamping webs face the side walls of associated containers.

10. The transport and packaging container according to claim 9, wherein the connecting webs are provided at lower ends of the receptacles for connecting the flexible clamping webs with each other.

11. The transport and packaging container according to claim 10, wherein the flexible clamping webs, bias respective opposite side walls of the receptacles elastically towards each other to enable clamping of containers with different diameters.

12. The transport and packaging container according to claim 10, wherein the flexible clamping webs are configured to press the receptacles of a supporting structure laterally apart, so that the flexible clamping webs with their indentations are pressed against circumferential sidewalls of the containers in the second position and the containers are accommodated with sufficient holding forces in the receptacles.

13. The transport and packaging container according to claim 12, wherein the carrier is configured to be pulled apart in transverse direction for transferring the carrier into a first position so that the containers may be removed from the receptacles without much effort or so that they can be displaced therein.

14. The transport and packaging container according to claim 13, further comprising form-fitting elements having an L-shaped profile are formed on outer walls of outermost hexagonal receptacles of the carrier, the form-fitting elements forming T-shaped receptacles, into which a correspondingly shaped latching rail is inserted, so that the carrier can be pulled apart for expanding all receptacles of the carrier by pulling latching rails in the transverse direction.

15. The transport and packaging container according to claim 6, further comprising that a majority of the bottoms of the containers are freely accessible from below the carrier while being accommodated in the receptacles of the carrier.

16. The transport and packaging container according to claim 6, wherein the receptacles are formed by a plurality of transverse webs extending in parallel with each other, which are connected to each other via S-shaped connecting webs disposed at regular intervals and extending substantially perpendicularly to the transverse webs for defining the regular arrangement, wherein all side walls of the receptacles can be adjusted in a coordinated manner from a first position to a second position upon displacement of the transverse webs by pivoting a first side of the carrier relative to a second side of the carrier opposite to the first side.

17. The transport and packaging container according to claim 6, wherein the carrier and/or the first segment is/are formed of a plastic material.

18. The transport and packaging container according to claim 6, wherein the carrier and/or at least the receptacles of the carrier and/or at least the bottom of the first segment is/are formed of a high-temperature-resistant plastic material, which is resistant to high temperatures of up to 330° C. or up to 350° C.

19. The transport and packaging container according to claim 18, wherein the high-temperature-resistant plastic material is a thermoplastic selected from a group consisting of: polyimide (PI), polyetherketone (PEK), polyetheretherketone (PEEK), polyetherketoneketone (PEKK) and polyetherketoneetherketoneketone (PEKEEK).

20. The transport and packaging container according to claim 1, wherein at least a bottom of the transport and packaging container is formed of a metal, wherein the metal is coated by a basic coating material consisting of $SiO_2$, $TiO_2$, $Al_2O_3$ or $ZrO_2$ and then tempered or burned.

21. The transport and packaging container according to claim 1, wherein the side walls of the first segment are provided at least partially with openings, which are closed by bonding a gas-permeable plastic foil.

22. A process for the thermal treatment of a plurality of containers for substances for medical, pharmaceutical or cosmetic applications, comprising:
providing a transport and packaging container accommodating the containers sterile sealed against the environment, the transport and packaging container comprising a first segment having a bottom and a plurality of upright side walls protruding perpendicularly from the bottom, and positioning devices for positioning the plurality of containers in interior of the transport and packaging container in a regular arrangement in such a manner that a collision of directly adjacent containers is prevented, wherein an upper end of the first segment opposite to the bottom and a side of the first segment is open to enable removal of the containers via the upper end or an open side of the first segment, and the upper end of the first segment and the open side of the first segment are covered by a protective foil so that the interior of the transport and packaging container is sterile sealed against the environment;
opening the transport and packaging container so that the interior of the transport and packaging container is accessible via the upper end and the open side of the first segment by drawing-off the protective foil from the first segment;
processing the containers while being supported on the bottom of the first segment or while being supported in a carrier, which is accommodated in the transport and packaging container in the step of providing the transport and packaging container, wherein the first segment is formed like a drawer having three upright side walls protruding perpendicularly from the bottom, and Wherein the protective foil is bonded to rims of the first segment for covering the upper end of the first segment and the open side of the first segment.

23. The process according to claim 22, further comprising:
closing the transport and packaging container by covering the upper end of the first segment and the side of the first segment with the protective foil.

24. The process according to claim 22, further comprising:
removing the carrier out of the transport and packaging container.

25. The process according to claim 24, further comprising:
inserting the carrier together with the containers after the step of processing the containers into the transport and packaging container.

26. The process according to claim 22, wherein the step of processing the containers further comprises:
processing the plurality of containers while being supported on the bottom of the first segment or while being supported in the carrier in a thermal processing station at temperatures of up to 330° C. or up to 350° C.

27. The process according to claim 26, wherein the processing of the plurality of containers is performed in a hot oven or hot tunnel at temperatures of up to 330° C. or up to 350° C., so that endotoxins and/or the lysis of bacteria and/or cytokine inducing substances (CIS) are removed thermally in the containers.

28. The process according to claim 26, wherein the processing of the plurality of containers is performed in a hot oven or hot tunnel at temperatures of up to 330° C. or up to 350° C., so that silicone layers are burned-in on inner surfaces of the containers.

* * * * *